United States Patent [19]

Kamen et al.

[11] Patent Number: 5,349,852
[45] Date of Patent: Sep. 27, 1994

[54] PUMP CONTROLLER USING ACOUSTIC SPECTRAL ANALYSIS

[75] Inventors: Dean L. Kamen, Bedford, N.H.;
Joseph B. Seale, Gorham, Me.;
Joseph Briggs, Manchester, N.H.;
Finn Arnold, Sutton, Mass.

[73] Assignee: Deka Products Limited Partnership, Manchester, N.H.

[21] Appl. No.: 792,877

[22] Filed: Nov. 15, 1991

Related U.S. Application Data

[63] Continuation-in-part of Ser. No. 615,612, Nov. 19, 1990, abandoned, Ser. No. 673,834, Mar. 22, 1991, abandoned, Ser. No. 674,813, Mar. 22, 1991, abandoned, and Ser. No. 614,806, Nov. 19, 1990, abandoned, each is a continuation-in-part of Ser. No. 523,801, May 15, 1990, Pat. No. 5,088,515, which is a continuation-in-part of Ser. No. 345,387, May 1, 1989, Pat. No. 4,976,162, which is a continuation-in-part of Ser. No. 92,481, Sep. 3, 1987, Pat. No. 4,826,482, which is a continuation-in-part of Ser. No. 22,167, Mar. 5, 1987, Pat. No. 4,808,161, and Ser. No. 836,023, Mar. 4, 1986, Pat. No. 4,778,451.

[51] Int. Cl.$^5$ ............. G01F 17/00; G01F 22/00; F04B 49/06; G05D 7/06
[52] U.S. Cl. ............. 73/149; 137/101.31; 364/510
[58] Field of Search ........... 73/149, 290 B, 290 V; 137/101.31; 417/279, 282, 379, 384, 390, 395; 364/510, 564

[56] References Cited

U.S. PATENT DOCUMENTS

| | | | |
|---|---|---|---|
| 2,491,418 | 12/1949 | Schlesman | 73/149 |
| 2,666,326 | 1/1954 | Poole et al. | 73/149 |
| 2,785,567 | 3/1957 | Poole et al. | 73/24.05 |
| 2,837,914 | 6/1958 | Caldwell | 73/589 |
| 2,998,723 | 9/1961 | Smith et al. | 73/290 |
| 3,075,382 | 1/1963 | Mathias | 73/149 |
| 3,110,890 | 11/1963 | Westcott et al. | 340/244 |
| 3,163,843 | 12/1964 | Dieckamp | 340/1 |
| 3,237,451 | 3/1966 | Haeff | 73/149 |
| 3,241,368 | 3/1966 | Newitt | 73/290 B |
| 3,252,325 | 5/1966 | Miller . | |
| 3,286,098 | 11/1966 | Long et al. | 250/230 |
| 3,312,107 | 4/1967 | Burns et al. | 73/149 X |
| 3,324,716 | 6/1967 | Roberts | 73/149 |
| 3,357,245 | 12/1967 | Wolfrum | 73/290 |
| 3,427,652 | 2/1969 | Seay | 166/250 |
| 3,494,185 | 2/1970 | Watanabe et al. | 73/149 |
| 3,540,275 | 11/1970 | Post et al. | 73/290 |
| 3,596,510 | 8/1971 | Seigel et al. | 73/149 |
| 3,683,212 | 8/1972 | Zoltan | 310/8.3 |

(List continued on next page.)

FOREIGN PATENT DOCUMENTS

| | | |
|---|---|---|
| 0119790 | 9/1984 | European Pat. Off. . |
| 2-51023 | 2/1990 | Japan . |
| 83/02001 | 6/1983 | World Int. Prop. O. . |

*Primary Examiner*—Tom Noland
*Attorney, Agent, or Firm*—Bromberg & Sunstein

[57] ABSTRACT

A system for controlling the flow of fluid through a line (3). The system may include first and second valves (A, B; and 6, 7) in the line (3). Between the first and second valves is located a chamber (52, 82), part of which may be filled with fluid having a variable volume (52), and another part of which is filled with a measurement gas (82, $V_1$), such as air. The chamber may be isolated from the pressure effects in the rest of the line by closing both valves. The valves may also permit fluid to flow into or out of the chamber. The second portion of the chamber has a common boundary with the first part in such a way that the combined volume of the first and second parts is constant. A loudspeaker (22, 33, 571) creates sound waves in the gas in the second part of the chamber, in order to measure the volume of the fluid in the first part. A controller directs the operation of the valves and controls positive and negative pressure sources, which may be used to create subsonic pressure variations to produce the desired flow. The volume measurement is achieved by acoustic volume measurement techniques.

15 Claims, 15 Drawing Sheets

U.S. PATENT DOCUMENTS

| | | | |
|---|---|---|---|
| 3,693,613 | 9/1972 | Kelman | 128/24 A |
| 3,769,834 | 11/1973 | Ogle | 73/149 |
| 4,072,046 | 2/1978 | Lao | 73/574 |
| 4,229,798 | 10/1980 | Rosie et al. | 364/564 |
| 4,303,376 | 12/1981 | Siekmann | 417/360 |
| 4,318,674 | 3/1982 | Godbey et al. | 417/36 |
| 4,341,116 | 7/1982 | Bilstad et al. | 73/290 V |
| 4,430,891 | 2/1984 | Holm | 73/149 |
| 4,474,061 | 10/1984 | Parker | 73/149 |
| 4,535,627 | 8/1985 | Prost et al. | 73/290 B |
| 4,561,298 | 12/1985 | Pond | 73/149 |
| 4,599,892 | 7/1986 | Doshi | 73/49.2 |
| 4,640,130 | 2/1987 | Sheng et al. | 73/579 |
| 4,651,555 | 3/2487 | Dam | 73/19 |
| 4,689,553 | 8/1987 | Haddox | 324/58.5 |
| 4,704,902 | 11/1987 | Doshi | 73/149 |
| 4,713,966 | 12/1987 | Thyren et al. | 73/149 |
| 4,754,186 | 6/1988 | Choperena et al. | 310/316 |
| 4,764,166 | 8/1988 | Spani | 604/65 |
| 4,778,451 | 10/1988 | Kamen | 73/149 X |
| 4,808,161 | 2/1989 | Kamen | 73/149 X |
| 4,811,595 | 3/1989 | Marciniak et al. | 73/149 |
| 4,818,186 | 4/1989 | Pastrone et al. | 417/63 |
| 4,821,558 | 4/1989 | Pastrone et al. | |
| 4,826,482 | 5/1989 | Kamen | 73/149 X |
| 4,842,584 | 6/1989 | Pastrone et al. | 604/50 |
| 4,874,359 | 10/1989 | White et al. | 604/4 |
| 4,899,573 | 2/1990 | Dimmick et al. | 73/49.2 |
| 4,927,411 | 5/1990 | Pastrone et al. | 604/65 |
| 4,944,191 | 7/1990 | Pastrone et al. | 73/599 |
| 4,949,584 | 8/1990 | Lade et al. | 73/865.8 |
| 4,971,516 | 11/1990 | Lawless et al. | 415/1 |
| 4,976,162 | 12/1990 | Kamen | 364/564 X |
| 4,991,433 | 2/1991 | Warnaka et al. | 73/149 X |
| 5,000,664 | 3/1991 | Lawless et al. | 417/63 |
| 5,211,201 | 5/1993 | Kamen et al. | 604/123 X |

…

PUMP CONTROLLER USING ACOUSTIC SPECTRAL ANALYSIS

This application is a continuation-in-part of application Ser. No. 615,612 filed Nov. 19, 1990, (for Acoustic Volume Measurement with Fluid Management Capability), and now abandoned, application Ser. No. 673,834 (for Membrane-based Peristaltic Pump), filed Mar. 22, 1991, and now abandoned, application Ser. No. 674,813 (for Fluid-Control Valve System), also filed Mar. 22, 1991, abandoned as file-wrapper continuing application Ser. No. 07/979,408 on Nov. 19, 1992, now issued as U.S. Pat. No. 5,241,985, and application Ser. No. 614,806 filed Nov. 19, 1990 (for Integral Intravenous Fluid Delivery Device), abandoned as file-wrapper continuing application Ser. No. 07/908,524 on Jun. 29, 1992, and now issued as U.S. Pat. No. 5,195,986 which are continuations-in-part of application Ser. No. 523,801 filed May 15, 1990 (for a Valve System with Removable Fluid Interface), issued Feb. 18, 1992 as U.S. Pat. No. 5,088,515, which is a continuation-in-part of application Ser. No. 345,387 filed May 1, 1989, issued Dec. 11, 1990 as U.S. Pat. No. 4,976,162 (for an Enhanced Pressure Measurement Flow Control System), which is a continuation-in-part of application Ser. No. 092,481 filed Sep. 3, 1987, issued as U.S. Pat. No. 4,826,482, which is a continuation-in-part of application Ser. No. 022,167 filed Mar. 5, 1987, issued as U.S. Pat. No. 4,808,161, and application Ser. No. 836,023 filed Mar. 4, 1986, issued as U.S. Pat. No. 4,778,451. Filed concurrently herewith is an application, Ser. No. 792,483, now issued as U.S. Pat. No. 5,211,201, for Intravenous Fluid Delivery System with Air Elimination by Kamen and Faust, and now U.S. Pat. No. 5,195,986. These related applications are hereby incorporated herein by reference.

TECHNICAL FIELD

The invention relates generally to systems that control flow through a line, and in particular intravenous fluid delivery systems.

BACKGROUND ART

It is known in the art to measure the free volume of a confined space by applying to the gas within the space repeated compressions of predetermined waveform by means of a diaphragm, for example, of a loudspeaker, and generating electrical signals representative of the resultant variation of pressure by means, for example of a microphone, and calculating the free volume of the confined space by measuring the electrical signals so generated. See, for example, U.S. Pat. Nos. 4,561,298, for an invention of Pond, and 3,237,451, for an invention of Haeff; these patents are hereby incorporated herein by reference. In accordance with this approach, a reference container of known volume may be disposed adjacent to the unknown volume, and a common loudspeaker at the boundary between the two volumes may be used to apply repeated compressions simultaneously to both volumes. The resultant pressure variations can then be monitored by microphones placed in each volume, and the electrical outputs from the two microphones may be compared to obtain a signal whose amplitude is representative of the unknown volume. Pond (col. 2, lines 26–29) teaches that the frequency of the repeated compressions should be sufficiently low to avoid problems associated with Helmholtz resonance.

The accuracy of volume measurement systems of the acoustic-pressure type disclosed in these two patents is dependent upon the degree to which differences between the two microphones can be eliminated or compensated and also upon the recalibration of the systems to take into account drift caused, for example, by changes in temperature and humidity or other pertinent characteristics of the system and of the air or other gas used in the measurement. The accuracy may also be adversely affected by gas leaks in the reference or unknown volumes.

SUMMARY OF INVENTION

In accordance with one embodiment, the invention provides a system for determining the volume of a chamber. The system includes an arrangement for associating with the chamber a resonatable mass of known acoustic characteristics so as to form an acoustic resonant system and an arrangement for determining the frequency of self-resonance of the system. In a preferred embodiment, the resonatable mass is achieved by use of a port affixed to the chamber, and self-resonance is achieved using a microphone and loudspeaker acoustically coupled to the resonant system and in electrical communication with one another.

In accordance with another embodiment of the invention, there is provided a system for controlling the flow of fluid through a line. Such a system includes first and second valves in the line between is located a chamber, part of which may be filled with fluid having a variable volume, and another part is filled with a measurement gas (such as air). The chamber may be isolated from the pressure effects in the rest of the line by closing both valves. The valves may also permit fluid to flow into or out of the chamber. The second portion of the chamber has a common boundary with the first part in such a way that the combined volume of the first and second parts is constant. There are also means for creating sound waves in the gas in the second part of the chamber, in order to measure the volume of the fluid in the first part, for directing the operation of the valves and for creating subsonic pressure variations to produce the desired flow. The volume measurement is achieved by acoustic volume measurement techniques.

The system determines a frequency of self-resonance of the system, and, based on the frequency of self-resonance, the volume of liquid in the chamber. In one embodiment the system controls the two valves according to a cycle comprising the steps of (i) closing the second valve, which leads to the line downstream of the chamber, (ii) opening the first valve, which leads to the line upstream of the chamber, (iii) then closing the first valve, after fluid has flowed into the chamber, (iv) then determining the volume of liquid in the chamber, (v) then opening the second valve, and (vi) then determining the volume of liquid left in the chamber, tracking the volume while fluid is flowing is flowing from the chamber, and/or determining the amount of fluid left in the chamber after the second valve is closed again.

To determine the volume of fluid in the chamber the controller generates an electrical signal having a spectrum of frequencies, which is converted through a loudspeaker into sound waves in the chamber. The acoustic response to the signal input into the chamber is picked up by a microphone. Based on the response the controller determines whether a frequency in the spectrum causes the resonatable mass to resonate, and calculates, based on a determined resonant frequency, the volume of liquid in the chamber. To determine the resonant frequency the controller measures the gain of the acoustic response relative to the electrical signal is measured at a plurality of frequencies in the spectrum. The controller may also measure the phase angle of the acoustic response relative to the electrical signal, in order to determine the resonant frequency. The controller may also detect the presence of a gas-bubble in the liquid by examining the phase and gain information.

BRIEF DESCRIPTION OF THE DRAWINGS

The foregoing features of the invention will be more readily understood by reference to the following description taken with the accompanying drawings, in which.

DETAILED DESCRIPTION OF SPECIFIC EMBODIMENTS

Figure 1:
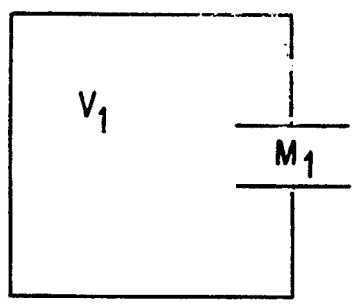
FIG. 1 is a schematic representation of an acoustic resonant system including a volume and an associated port.

Turning now to FIG. 1, there is shown a schematic representation of an acoustically resonant system including a chamber having a volume $V_1$ and an associated port $M_1$. Assuming that the system employs air as the gas in the chamber, it is known in the art that such a system has a resonance at frequency $f_o$ given by the formula $$f_o = \frac{1}{\sqrt{\left(\frac{\rho_o L}{S}\right)\left(\frac{V_1}{\gamma P_o}\right)} \cdot 2\pi} \tag{1}$$

where
$\rho_o$=the density of air in the system,
$S$=the cross sectional area of the port $M_1$,
$L$=the length of the port $M_1$,
$P_o$=barometric pressure of the air in the system, and
$\gamma$=constant for adiabatic compression.
If $f_o$ is known, $V_1$ is given by $$V_1 = \left(\frac{\gamma S}{L}\right)\left(\frac{1}{4\pi^2 f_o^2}\right)\left(\frac{P_o}{\rho_o}\right). \tag{2}$$

If furthermore $V_1$ and $f_o$ are known, the ratio $(P_o/\rho_o)$ can be determined as $$\frac{P_o}{\rho_o} = \frac{V_1 4\pi^2 f_o^2 L}{\gamma S}. \tag{3}$$

These equations can be used in the manner described below with respect to certain embodiments of the invention to determine an unknown volume.

Figure 2:
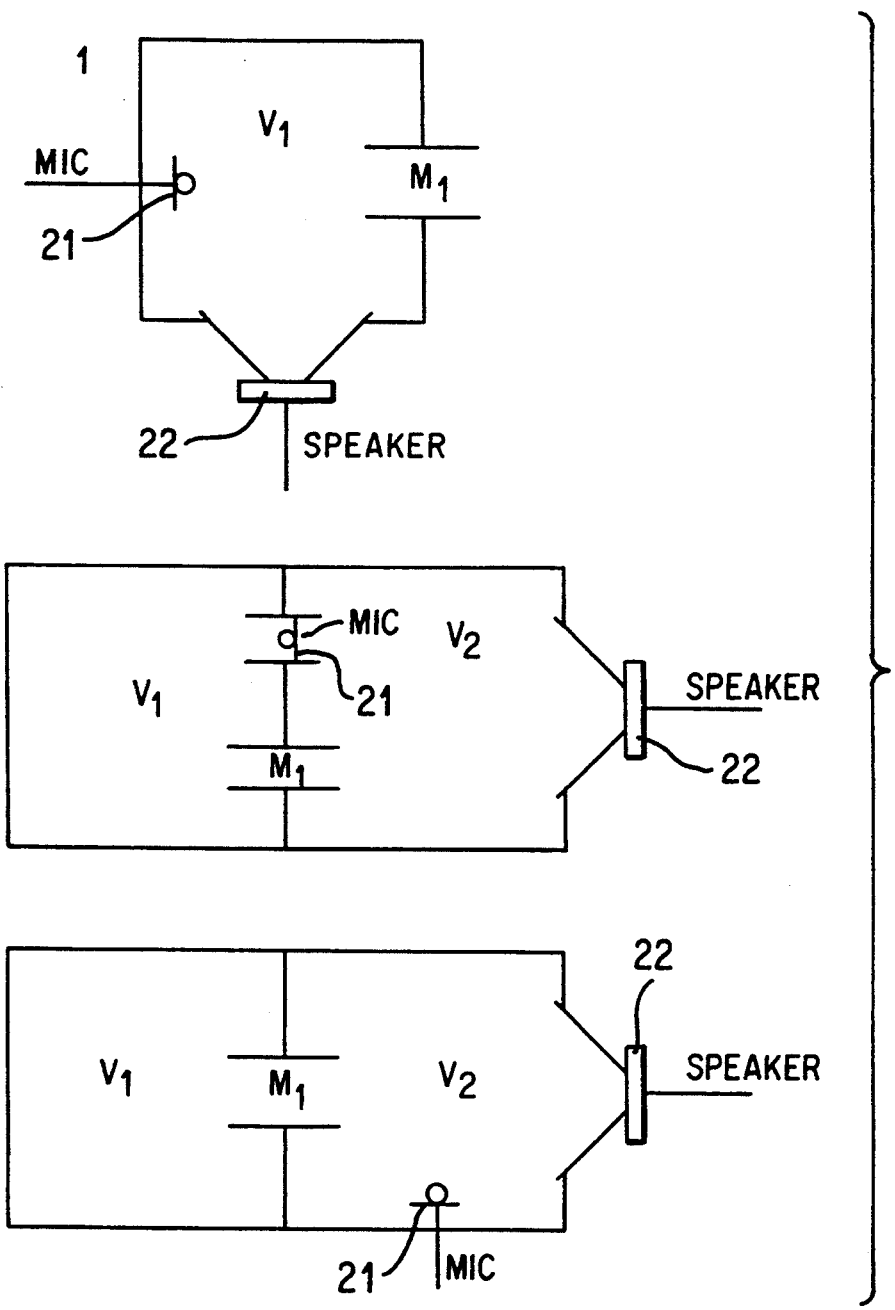
FIG. 2 presents schematic representations of three embodiments of the invention for measurement of the volume $V_1$ using self-resonance.

In FIG. 2 are shown schematic representations of three embodiments of the invention that utilize self-resonance for determination of the volume of a chamber. In each case, the chamber has a volume $V_1$, and there has been associated with the chamber a port $M_1$ to form an acoustic system of the type described in connection with FIG. 1. Microphone 21 (or other suitable acousto-electrical transducer) and a loudspeaker 22 (or other suitable electro-acoustical transducer) are acoustically coupled to this acoustic system. The electrical output of the microphone is placed in communication with the electrical input of the loudspeaker 22, in such a way that the amplitude and phase relationships of the signals promote acoustic resonance of the system. (A suitable circuit for achieving such acoustic resonance is discussed below in connection with FIG. 4.) Measurement of a quantity related to the frequency $f_o$ of self-resonance of the system can permit determination of the volume in accordance with equation (2) set forth above. Such a frequency measurement may be achieved in a microprocessor circuit, for example, by counting the number of clock pulses in a period of the self-oscillation signal; this count can then be used by the microprocessor to implement the calculations of equation (2). In using equation (2), the ratio $(P_o/\rho_o)$ can be entered manually into the microprocessor. Alternatively, an additional chamber of known volume, configured with a port in a manner similar to one of the embodiments of FIG. 2, may be employed to produce self-resonance, and a quantity related to the frequency of this self-resonance may be measured in the manner just described. Then with knowledge of $V_1$ and $f_o$, the ratio ($P_o/\rho_o$) can be determined using equation (3), and this value may be used in equation (2) in determining the unknown volume.

In the simplest case, embodiment (1) of FIG. 2, the microphone is placed within the chamber and the loudspeaker forms a portion of the wall of the chamber. However, because the self-resonance technique described herein does not require that the chamber be sealed in the fashion required for acoustic-pressure type systems, the transducers employed in these embodiments do not need to be located in the chamber forming part of the self-resonant system. It is necessary only that the transducers be acoustically coupled to the system. In embodiments (2) and (3) of FIG. 2, a second volume $V_2$ is associated with the system and coupled to volume $V_1$ via the port $M_1$. In order for the equations set forth above to remain accurate, it is assumed that $V_2 \gg V_1$; however, if this is not the case, the effects of $V_2$ may be readily calculated by those skilled in the art. In each of embodiments (2) and (3) the loudspeaker 22 forms a portion of the wall of volume $V_2$. Such a configuration is beneficial when volume $V_1$ is too small to permit ready mounting of the loudspeaker, and can also permit the loudspeaker to serve in a second system employed in tandem, for example, as discussed below in connection with FIG. 3. In embodiment (2), the microphone 21, here preferably of the velocity type, forms a part of the wall between volumes $V_1$ and $V_2$ and responds only to differences in pressure between the two volumes; because the pressure differences between the two volumes tend to be near zero at frequencies below the frequency of natural resonance of the system, noise in the microphone is effectively canceled out. In embodiment (3), the microphone is disposed in volume $V_2$; the microphones in embodiments (1) and (3) are preferably of the pressure type. The use of the second volume $V_2$ protects the area surrounding the opening of the port $M_1$ to prevent disturbance of the air flow, clogging, and dust that would affect resonance. The second volume also isolates the combined $V_1$—$V_2$—$M_1$ system, including the microphone, from the environment.

Although the embodiments of FIG. 2 have been described in connection with a port $M_1$ associated with the chamber of volume $V_1$, it is necessary only to associate any resonatable mass of known acoustic characteristics to form a resonant system that includes the chamber, and methods analogous to those described above may be used to determine $V_1$ and the ratio ($P_o/\rho_o$).

Figure 3:
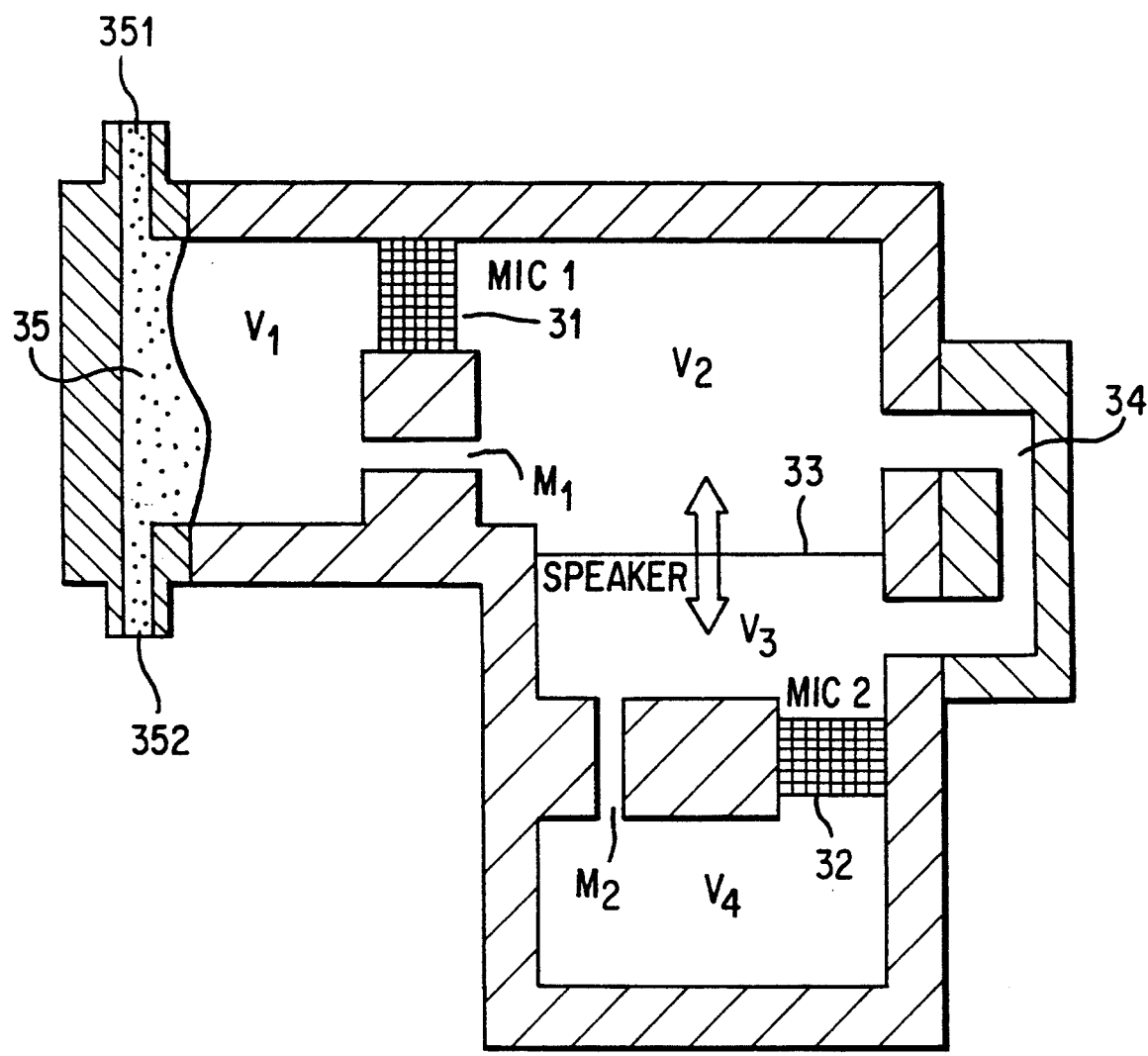
FIG. 3 illustrates schematically an embodiment of the invention utilizing a pair of embodiments of the type shown in FIG. 2 to produce a system for volume measurement in which differences between the two microphones as well as any drift caused by changes in the measurement gas characteristics or in other parts of the system may be automatically compensated.

As mentioned above, it is possible to use a pair of the embodiments (regardless whether or not such embodiments happen to be the same type) illustrated in FIG. 2 to determine an unknown volume and to determine the gas constant $P_o/\rho_o$ necessary for the volume calculation. FIG. 3 illustrates the use of a pair of the second FIG. 2 embodiments configured in tandem for this purpose. In this case it is desired to know the volume of fluid in variable volume 35 in order to control the flow of fluid along a path that includes inlet 351, volume 35, and outlet 352. (The use of volume measurement using acoustic resonance for the purpose of fluid flow control is discussed in further detail below in connection with FIGS. 7 and 8.) Because the total of volume 35 and volume $V_1$ remains constant, the determination of $V_1$ permits the determination of volume 35. In this arrangement, one resonant system of the second embodiment of FIG. 2 is formed with $V_1$, $M_1$ and $V_2$ and a second resonant system of the second embodiment of FIG. 2 is formed with $V_3$, $M_2$ and $V_4$. A conduit 34 (not drawn to scale) conducts low frequency (i.e. those not associated with self-resonance) pressure changes between chambers $V_2$ and $V_3$. The loudspeaker 33 is selectively switched into a circuit permitting alternately the self-resonance of each resonant system. Because $V_3$, $M_2$ and $V_4$ are all fixed, it is clear from equation (1) that the only factor affecting the resonant frequency of the second resonant system is a change in the ratio $P_o/\rho_o$. Thus the resonant frequency of the second resonant system is used in determining the ratio $P_o/\rho_o$, which in turn is used in the calculation of the volume $V_1$ in based on the resonant frequency of the first system.

In the embodiment of FIG. 3 (and that of FIGS. 7 and 8), piezo crystal loudspeakers may be advantageously employed because their rigidity provides good isolation between the volumes (to minimize the affect of one volume on resonance of the system employing the other volume) between which they are disposed and because they are relatively efficient and inexpensive. Electret microphones are advantageous because they are sensitive, relatively low-noise, relatively inexpensive, and can configured to measure either pressure or velocity. The speaker and the microphone should have resonant frequencies sufficiently higher than the resonant frequency of the acoustic resonant system. Foam rubber may be used advantageously to damp out standing waves in the main chambers. In cases where the variable volume $V_1$ results from the displacement primarily of one wall, it is preferable that the port $M_1$ be disposed with its long axis transverse to the direction of displacement of the wall.

Figure 4:
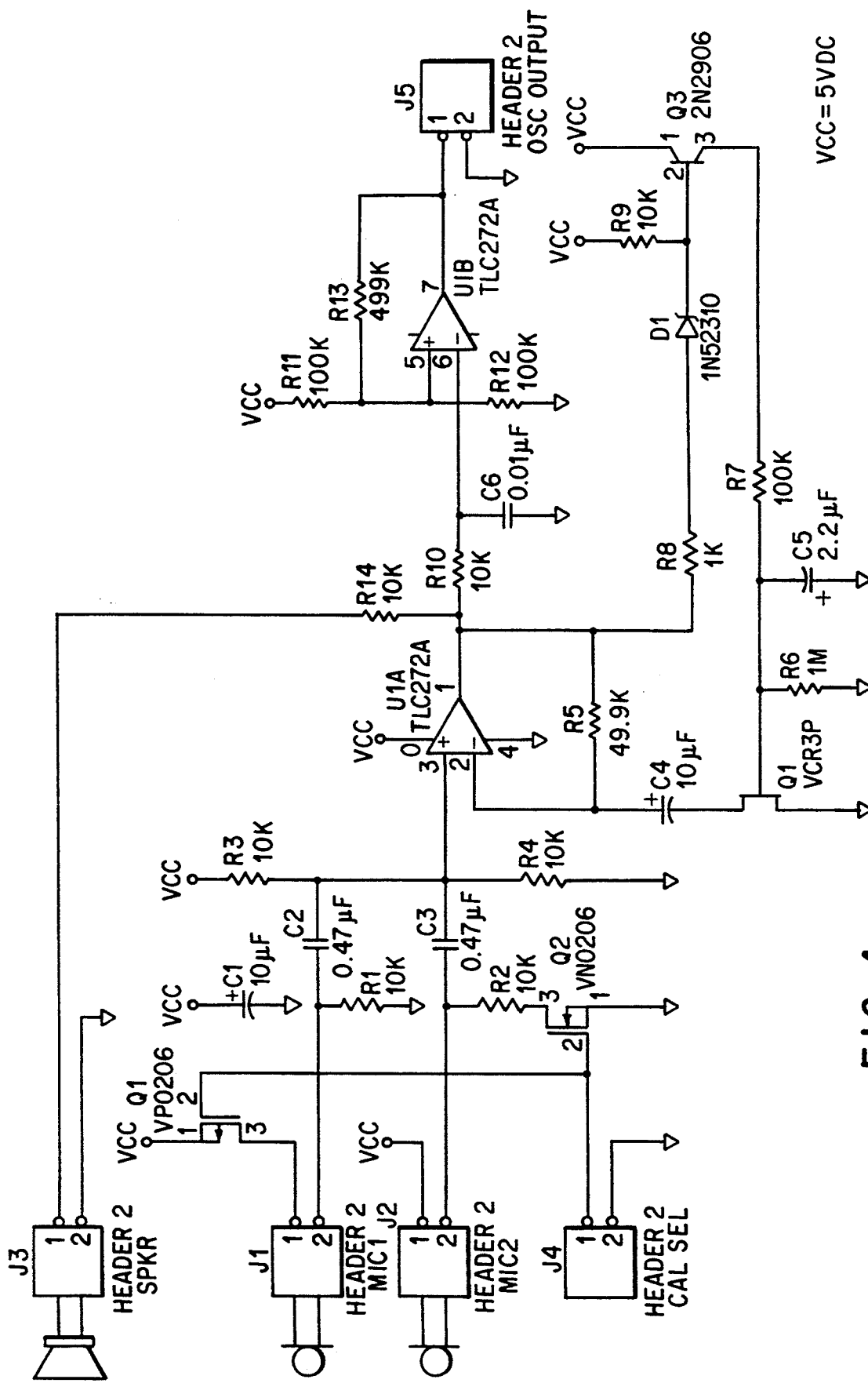
FIG. 4 is an electrical schematic of a circuit for driving the loudspeaker and connecting the microphones of the embodiments shown in FIGS. 3 and 7.
Figure 7:
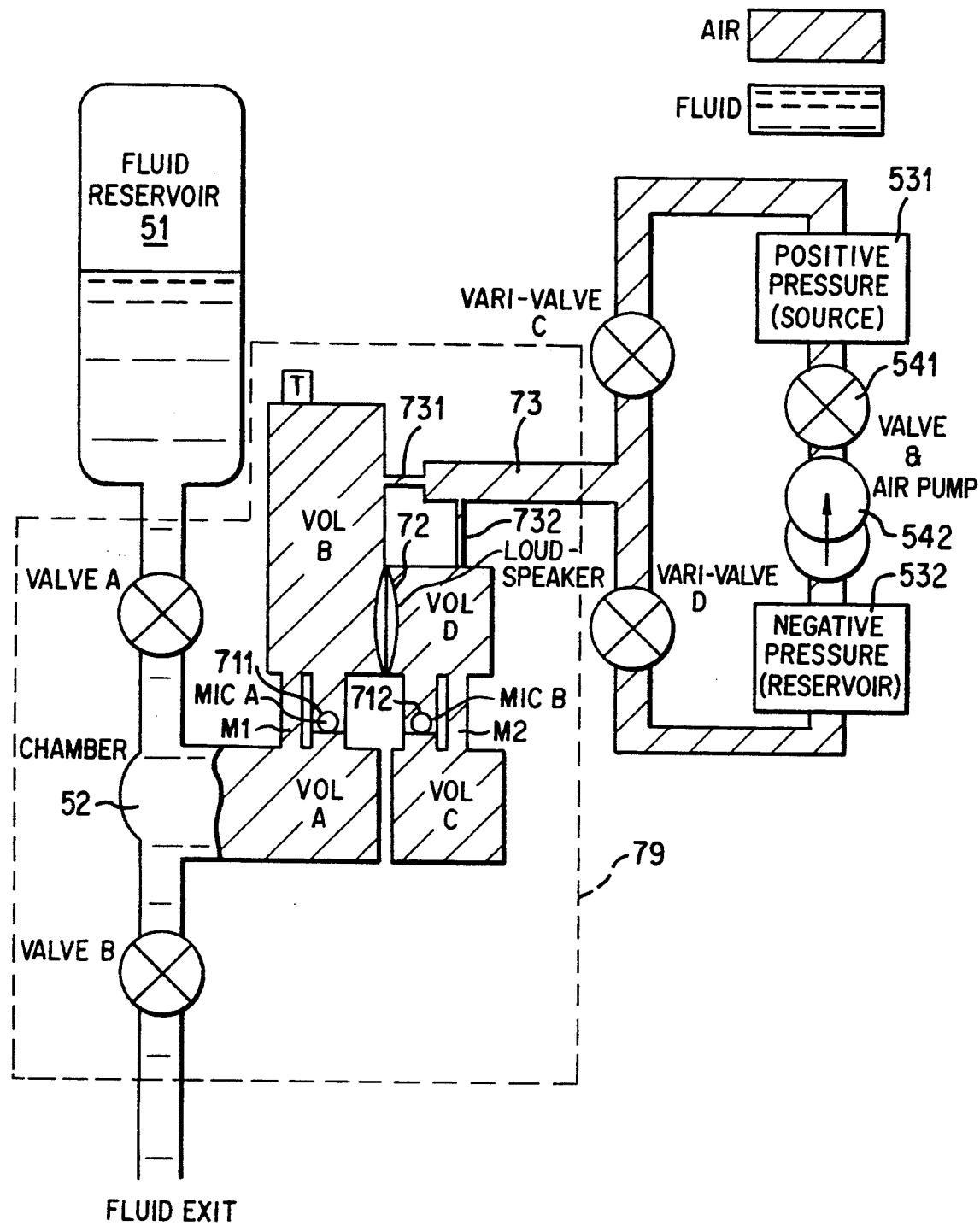
FIG. 7 is a schematic representation of another embodiment of the invention providing a fluid management system employing an acoustic resonance volume measurement system of the general type shown in FIG. 3.
Figure 8:
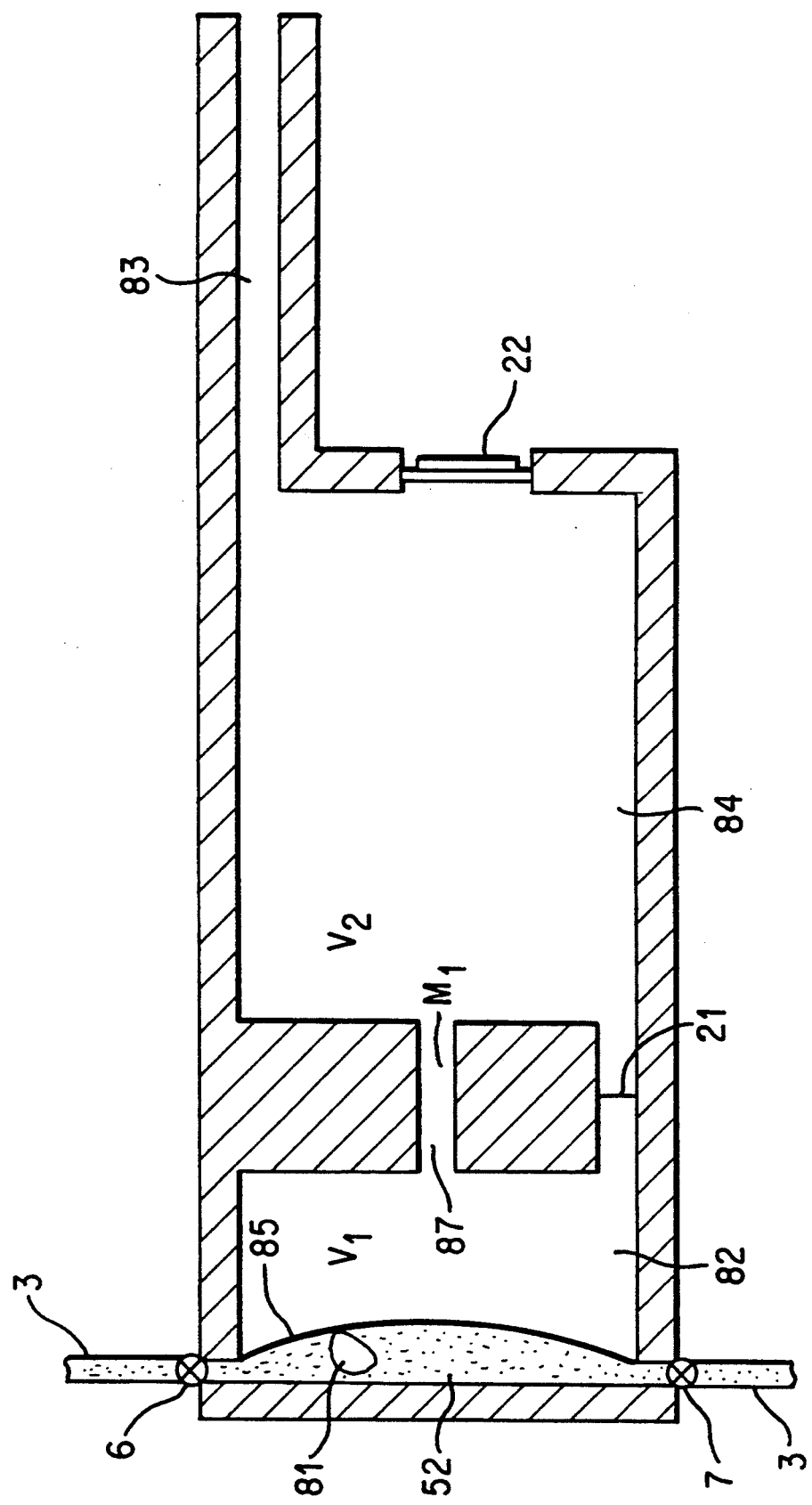
FIG. 8 shows another acoustic resonant system designed to control the flow of fluid through a line.

FIG. 4 is a schematic of a circuit suitable for effecting self-resonance measurements in accordance with the embodiments of FIGS. 3, 7, and 8. The FETs Q1 and Q2 are alternately switched into conducting and non-conducting states depending on the state of a signal from a microprocessor system obtained as an input from jack J4, and in this manner, the microprocessor selects whether MIC1 (connected via J1) or MIC2 (connected via J2) is live. The microphone signal is coupled via C2 or C3, depending on the microphone, to the amplifier circuit utilizing U1A, the output of which drives the loudspeaker through J3. Automatic gain control is provided when the voltage across zener diode D1 exceeds a threshold via Q3 and Q1. The oscillation resulting from the proximity of the loudspeaker and microphone in the acoustic resonant system described above in connection with FIGS. 1-3 is generally sinusoidal, and in the applications described below is at approximately 1 kHz. Although a sinusoid is a desirable waveform for the resonance, since it is substantially free of harmonics, it is not well suited to use in digital calculations. Accordingly a Schmitt trigger circuit associated with U1B provides a square wave output over J5 at the frequency of resonance. The frequency determination is made utilizing clock pulses running in the vicinity of 1 to 10 MHz, and the number of clock pulses occurring in duration of a signal pulse from the output over J5 is counted and stored. In one embodiment, 100 signal pulses are clocked, and the clock counts are stored and sorted by magnitude. The top and bottom 30 counts are discarded and the middle 40 counts are then averaged. At a 10 MHz clock, therefore, the frequency determination can be made relatively noise immune while still providing an output ten times per second.

Figure 5:
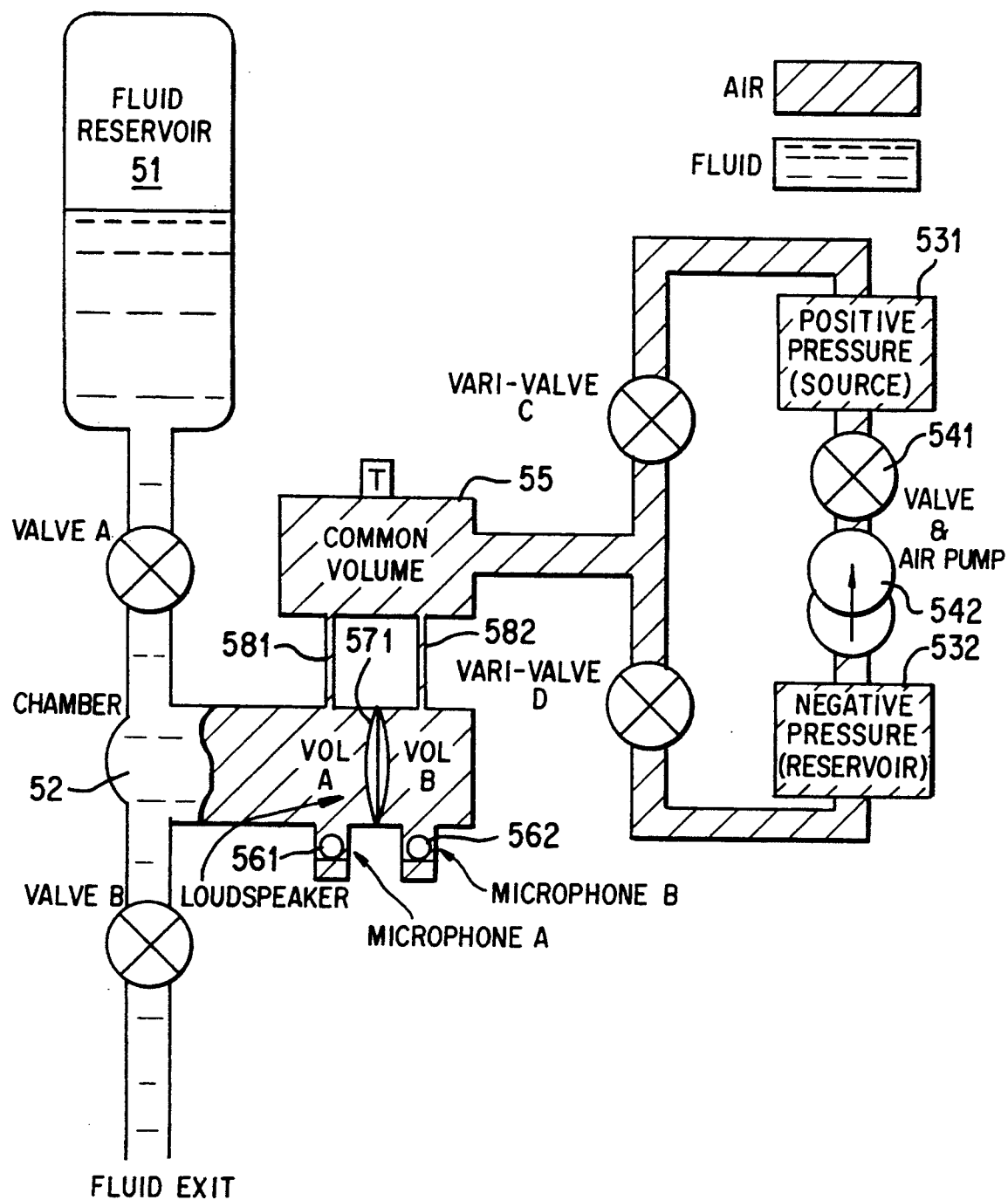
FIG. 5 is a schematic representation of an embodiment of the invention providing a fluid management system, capable of pumping fluid and controlling fluid flow, employing an acoustic-pressure volume measurement system.
Figure 6:
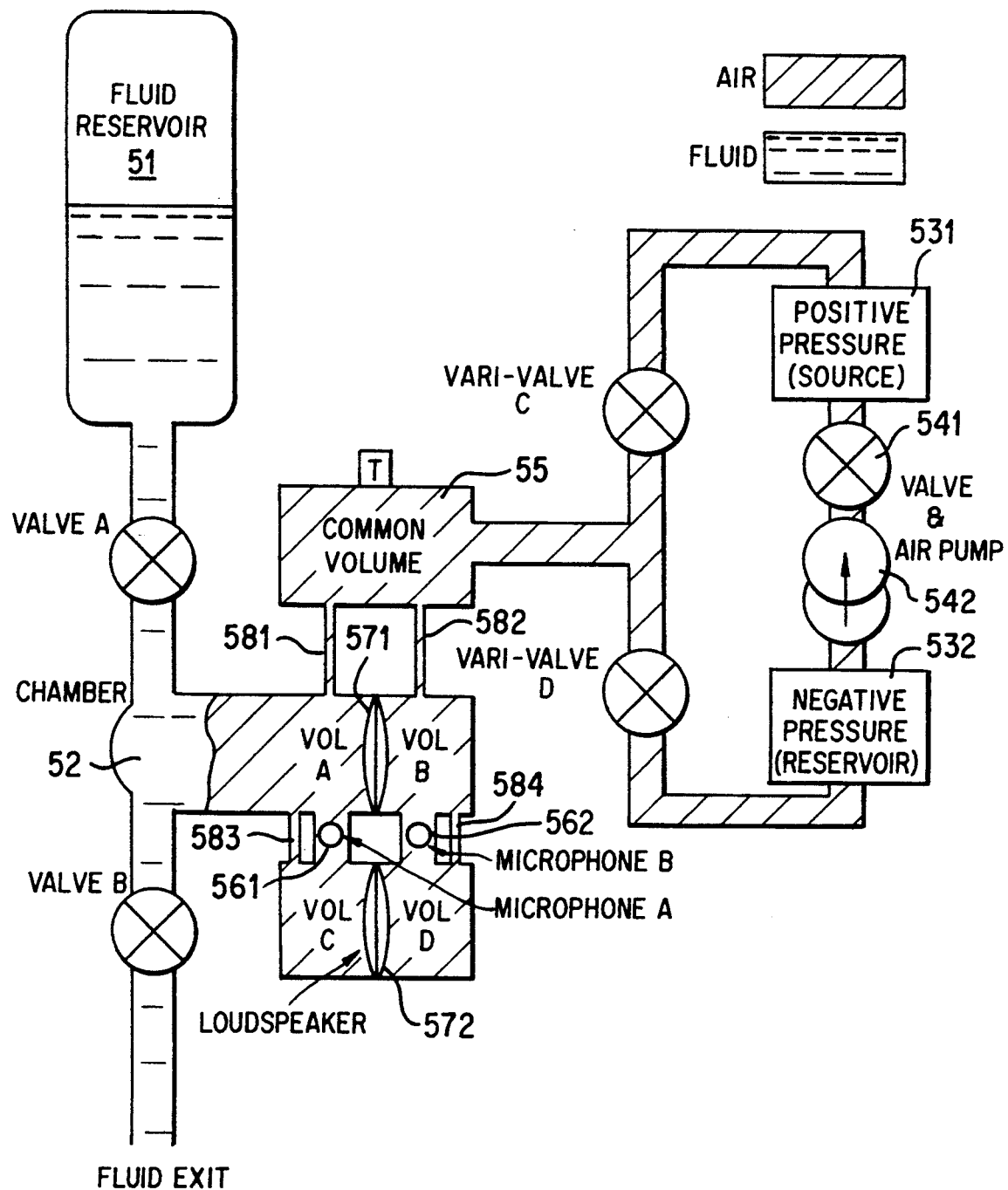
FIG. 6 is a schematic representation of a further embodiment of the invention providing a fluid management system employing an acoustic-pressure volume measurement system that uses differentially driven microphones and a duplexed reference volume arrangement to permit automatic compensation for microphone differences and system drift.

FIGS. 5 through 7 illustrate the manner in which acoustic volume measurement systems may be used to pump and to control the flow of fluid in accordance with the present invention. In this connection, the fluid management system in accordance with the present invention utilizes valves A and B, chamber 52, and an air system to displace the variable volume of the chamber 52 in the manner disclosed in U.S. Pat. No. 4,976,162 referred to above and in its predecessor applications. Fluid from reservoir 51 may be permitted to enter the chamber 52 when valve A is open and may be permitted to leave the chamber 52 when valve B is open, the actual flow being a function of pressure in chamber 52 and area surrounding as determined by the air system. The air system includes positive and negative pressure sources 531 and 532 respectively, air pump and valves 541 and 542 respectively for charging the pressure sources, and valves C and D for determining the pressure from the air system output presented to the chamber 52. Transducer T monitors the pressure in the chamber 52. The pumping and controlling cycles that are described in U.S. Pat. No. 4,976,162 and its predecessor applications are fully applicable to the present fluid management system. Indeed, because the present invention permits monitoring of the volume chamber 52 on a substantially continuous basis, any desired pumping or control cycle may be implemented with even greater flexibility than in the case of U.S. Pat. No. 4,976,162.

In FIG. 5 an acoustic-pressure type measurement system of the general type described above in Background Art is here used in a fluid management system in accordance with the present invention. The air system delivers air of a desired pressure via the common volume 55 and volume A to the interface with the chamber 52. Volume B serves as a reference volume in relation to variable Volume A. Compressions caused by loudspeaker 571 are detected by microphones 561 and 562 in volumes A and B respectively, whose outputs are then compared to arrive at a value for Volume A. The conduits 581 and 582 are designed to minimize the possible effect of resonance and to isolate Volumes A and B respectively.

In FIG. 6, fluid management is also achieved using an acoustic-pressure type measurement system; however, in this embodiment, there is provided an acoustic-pressure type measurement presenting important improvements over the prior art. In this embodiment, microphones 561 and 562 detect only pressure differentials between Volumes A and C on the one hand and B and D on the other, thus providing substantial noise cancellation. As in the case of conduits 581 and 582, the conduits 583 and 584 pass low frequency changes in pressure but otherwise preserve the isolation of the volumes to which they are coupled. Variations in sensitivity of microphones 561 and 562 can be compensated automatically by use of Volumes C and D in connection with loudspeaker 572. These two volumes are designed to be equal (or in any other predetermined ratio), so that any variation in the output of the two microphones when loudspeaker 572 is driven is attributable to differences in sensitivity of the microphones, and can be compensated automatically. By driving loudspeakers 571 and 572 at substantially different frequencies, compensating signals (derived from filtering the microphone outputs for the signal frequency used in relation to Volumes C and D) can be utilized on a continuous basis for the equalization of the outputs of the microphones in connection with the volume measurement determinations made with respect to Volumes A and B.

FIG. 7 illustrates the use of an acoustic resonance volume measurement system, of the type discussed above in connection with FIG. 3, in a fluid management system in accordance with the present invention. In this case chamber 52 corresponds to variable volume 35, and $V_1$, $V_2$, $V_3$, and $V_4$ correspond to Volumes A, B, D, and C respectively. Air pressure from the air system is delivered over conduits 73 and 731 to Volume B and chamber 52. Conduit 732, along with conduits 73 and 731, corresponds to the conduit 34 of FIG. 3 to equalize static pressure in the system. Measurement of Volume A is exactly as described above for measurement of volume $V_1$. Although FIG. 7 illustrates the use of the FIG. 3 embodiment of an acoustic resonance volume measurement system, it will be apparent that any of a variety of acoustic resonance volume measurement systems may be employed. For example, a simpler system may employ only Volumes A and B, and dispense with Volumes C and D and microphone 712, or may, for example, use any other of the embodiments shown in FIG. 2.

The use of an acoustic resonance volume measurement system in connection with a fluid management system offers some significant advantages over acoustic-pressure systems for volume measurement. First, pressure leaks that may inhere in the volumes have reduced impact on the measurement, and second, transducers may be more flexibly located.

FIG. 8 shows the embodiment (3) of FIG. 2 modified so as to control flow through a line 3, and with the microphone mounted in a different position. The back chamber 84 ($V_2$) is connected to an air supply line 103 that can be connected to positive and negative pressure sources, as shown in FIGS. 5–7 above. The air supply line 103 is narrow and long enough, so that it presents a substantial acoustic impedance, thereby preventing a significant amount of acoustic energy from escaping the back chamber 84. Valves 6 and 7, when they are both closed, isolate the fluid 52 in the front chamber 82 from pressure effects in the rest of the line 3.

The speaker 22 introduces acoustic energy to chambers 82 and 84 ($V_1$ and $V_2$), which are connected by an orifice 87 (which contains the resonatable mass $M_1$). The microphone 21 measures the response of the chamber-orifice-chamber system to the acoustic energy introduced by the speaker 22. By introducing a range of frequencies to the chamber-orifice-chamber system and analyzing the characteristics of the spectrum of frequencies detected by the microphone 21, the resonant frequency of the system may be determined. Such an analysis can also determine the presence of gas bubbles 81 in the liquid 52 in the front chamber 82.

Figure 9:
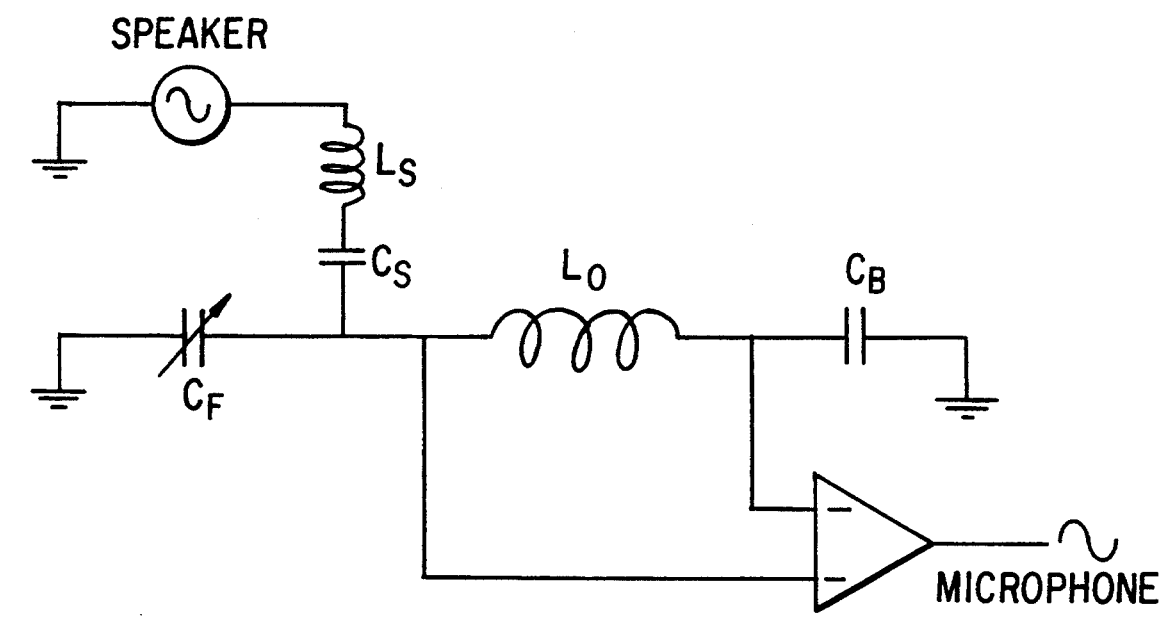
FIGS. 9 and 10 show electrical and mechanical models of the acoustic system shown in FIG. 8.
Figure 10:
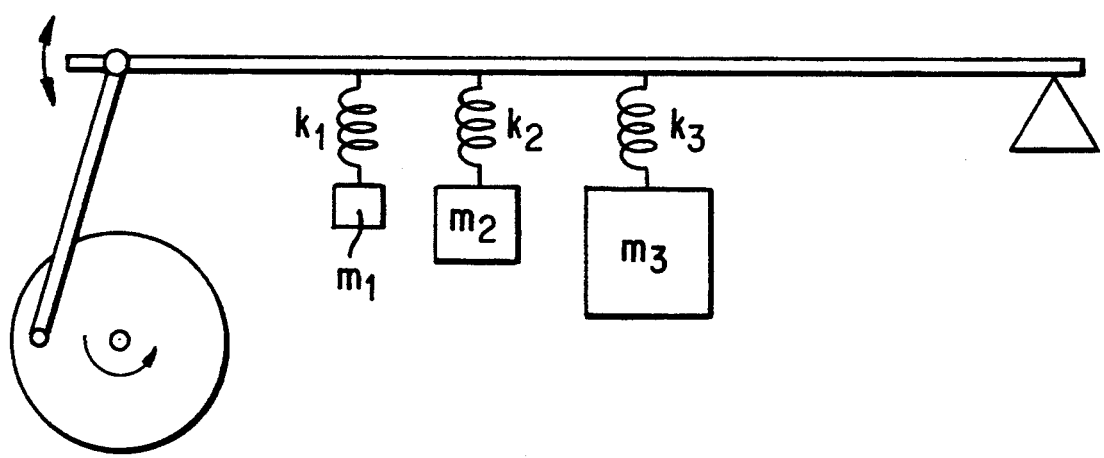

FIGS. 9 and 10 show electrical and mechanical models respectively of the acoustic chamber-orifice-chamber system of FIG. 8. In FIG. 9 the speaker is modeled by an AC source and may have associated with it an inductance, $L_S$, and a capacitance, $C_S$. Variable capacitor $C_F$ represents the gas-filled portion of the front chamber ($V_1$), which has a varying volume. Capacitor $C_B$ represents the back chamber ($V_2$), which has a constant volume. The inductance coil $L_O$ represents the orifice 87, which connects the front and back chambers. The op-amp measuring the voltage across the inductance coil $L_O$ represents the microphone. This is a simplified model, and a more accurate model of the acoustic chamber-orifice-chamber system would include resistors and additional capacitors and inductance coils. One can determine the resonant frequencies of this electrical system by comparing for various frequencies the gain and the phase shift of the output of the op-amp with respect to the AC source. One would expect two resonant frequencies for this electrical model, one associated primarily with $C_F$—$L_O$—$C_B$, the other being associated with the capacitance and inductance of the speaker.

FIG. 10 shows a mechanical system having three resonant frequencies. This system includes an oscillating lever driven by a rotating wheel, and three masses, $m_1$, $m_2$ and $m_3$, suspended from the lever by three springs, having spring constants $k_1$, $k_2$ and $k_3$. There is a resonance associated with each mass-spring system, proportional to $(k/m)^{\frac{1}{2}}$.

Like the mechanical system shown in FIG. 10, the acoustic system depicted in FIG. 8 has three resonant frequencies, one is associated with the speaker 22, another is associated with the gas bubble 81 in the liquid 52, and the third is associated by the geometry of the chamber-orifice-chamber system. The resonant frequency associated with the speaker does not change significantly. The resonant frequency associated with the bubble varies depending on the size of the bubble. The resonant frequency associated with the chamber-orifice-chamber geometry varies depending on the volume of gas in the front chamber ($V_1$).

Figure 11:
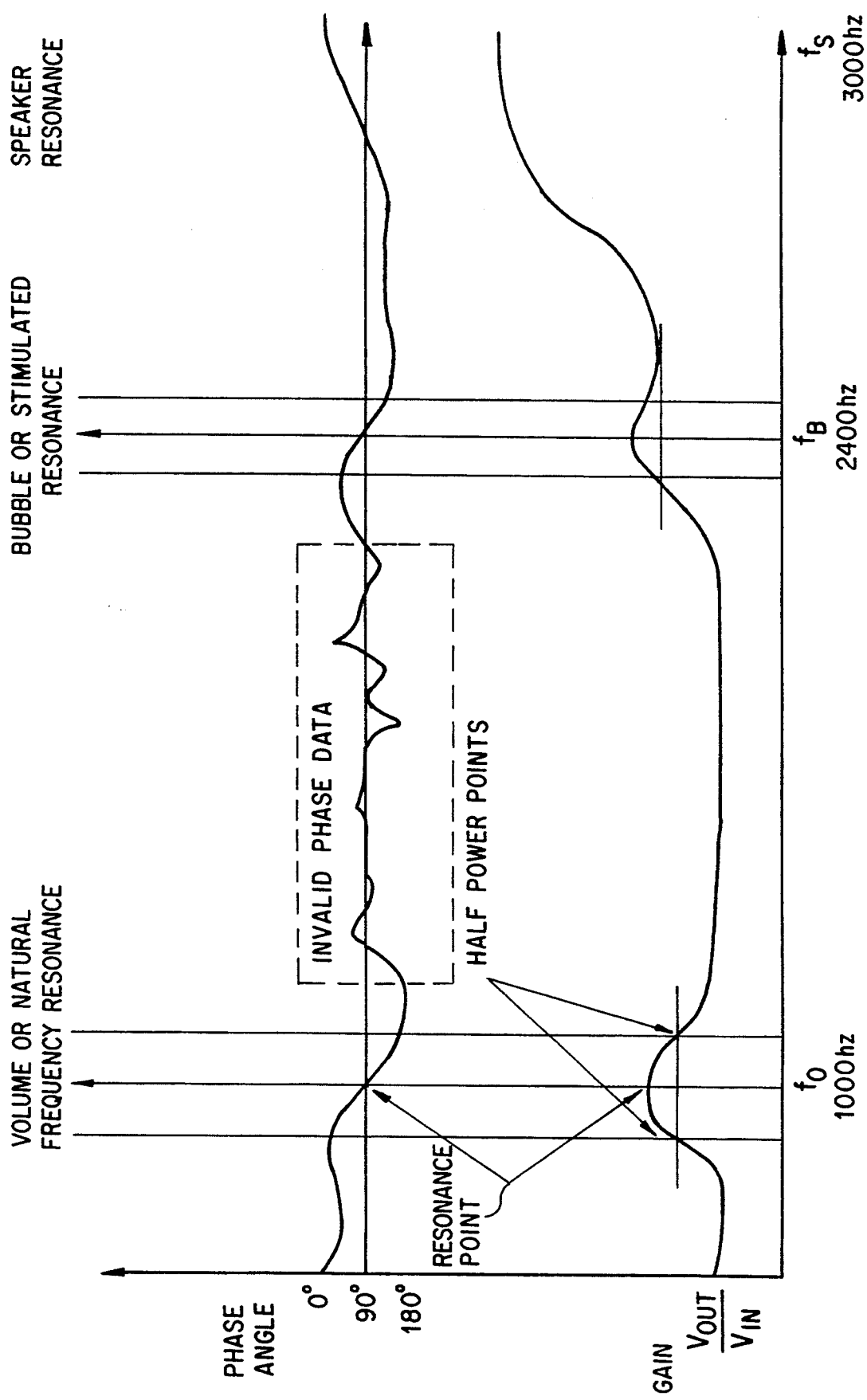
FIG. 11 shows plots of the phase angle and gain of the acoustic response of the acoustic system shown in FIG. 8, when the loudspeaker applies a range of frequencies to the system.

As noted above, to determine the resonant frequencies of the system, a spectrum of frequencies may be introduced into the system through the speaker, and the system's response may be detected by the microphone. An example of such a response is shown in FIG. 11, which plots the phase shift and gain for each frequency of the response. The phase shift and gain for a given frequency are measured with respect to the phase and amplitude of the signal applied to the speaker at that frequency. If at a certain frequency, the gain has a gaussian pulse and the phase shift is 90°, that frequency is resonant. The plot shown in FIG. 11 shows two resonant frequencies and part of a third. The resonant frequency associated with the chamber-orifice-chamber geometry is at about 1 kHz, the resonant frequency associated with the air bubble is at about 2.4 kHz, and the resonant frequency associated with the speaker is at the far right of the plot, at about 3 kHz The microphone also has a resonant frequency associated with it, but being about 10 kHz it is higher than even the speaker's resonant frequency. Between 1 kHz and 2.4 kHz the phase shift passes through 90° at several places; however, none of these points is associated with a peak in gain, and therefore none of these points represents a resonant frequency.

The quality factor, or Q, of a resonance is a measure of the sharpness of the peak, and is the ratio of the center frequency to the bandwidth, which is the frequency difference between the two half-power points. The Q for the volume and bubble resonances is about 12, whereas the speaker's is very low, due to its broad bandwidth. If the bubble 81 is very small it may not be possible to locate its high-side half-power frequency. If the bubble 81 is very large, it may spread across the membrane 85 and communicate with the gas in the front chamber 82, so that the peaks representing the volume and bubble resonances merge.

If a bubble is detected, it may be removed from the liquid 52 in the chamber. This may be done by means of the system shown and described in the patent application for Intravenous Fluid Delivery System with Air Elimination, Ser. No. 792,483, which is identified above and is filed concurrently herewith. In the system described therein, a return line is connected to the line 3 downstream of the chamber 82. This return line may be connected to the fluid reservoir, so that fluid can be pumped out of the chamber back to the reservoir, carrying with it any bubbles. Once the bubbles have been removed from the chamber, acoustic energy having a spectrum of frequencies can again be introduced into the chambers and another spectral analysis performed. If the spectral analysis shows no bubbles, then the frequency of volume resonance may be determined.

The resonance detection system scans a frequency spectrum through the speaker into the back chamber 84, and collects phase and gain information at each frequency. The collected information is stored in an array having three fields, for frequency, gain and phase. This array is then processed to identify the center frequency and Q for each resonance detected.

The signal processing hardware that is used to determine the resonant frequencies includes a sine-wave generator for injecting acoustic energy into the chamber, a peak detector for determining the gain, and a phase detector for measuring the phase angle between the input and output signals.

Figure 12:
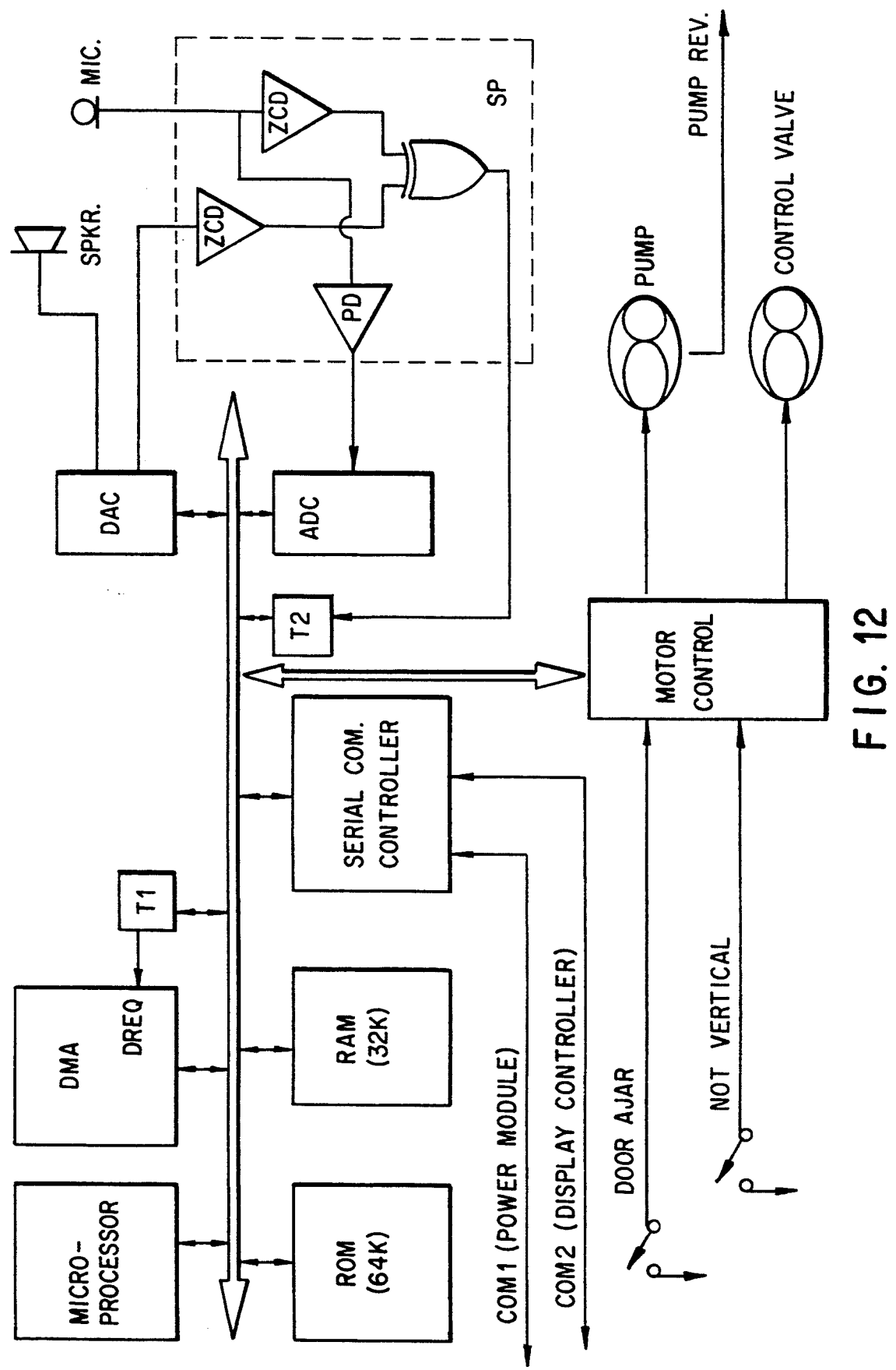
FIG. 12 is a block diagram of the signal processing and control elements of the pump controller.

Referring to FIG. 12, which shows elements of a preferred embodiment of the pump controller system, including elements of the resonance detection system. The resonance detection system uses sine-wave generator, which includes timer T1 that submits a 'request' to a direct memory access (DMA) controller. The DMA controller then reads a value from a stored sine table and forwards the value to a digital-to-analog converter (DAC). The sine table has sixteen periods. When the DMA controller comes to the end of the sine-wave table, it receives an end-of-cycle signal and returns to the beginning of the table. The frequency of the generated sine-wave can be altered by changing how fast T1 ticks; the faster T1 ticks, the higher the frequency. The rate that T1 triggers is set by the microprocessor, which forwards a value, $\tau_\theta$, depending on the desired frequency. ($\tau=2\pi/\omega$, $\omega=2\pi f$.) T1 is clocked by an 8 MHz crystal, and thus, in the region where the volume resonance is expected (around 1 kHz), the sine-wave frequency can be altered by increments of 0.125 Hz.

Figure 13:
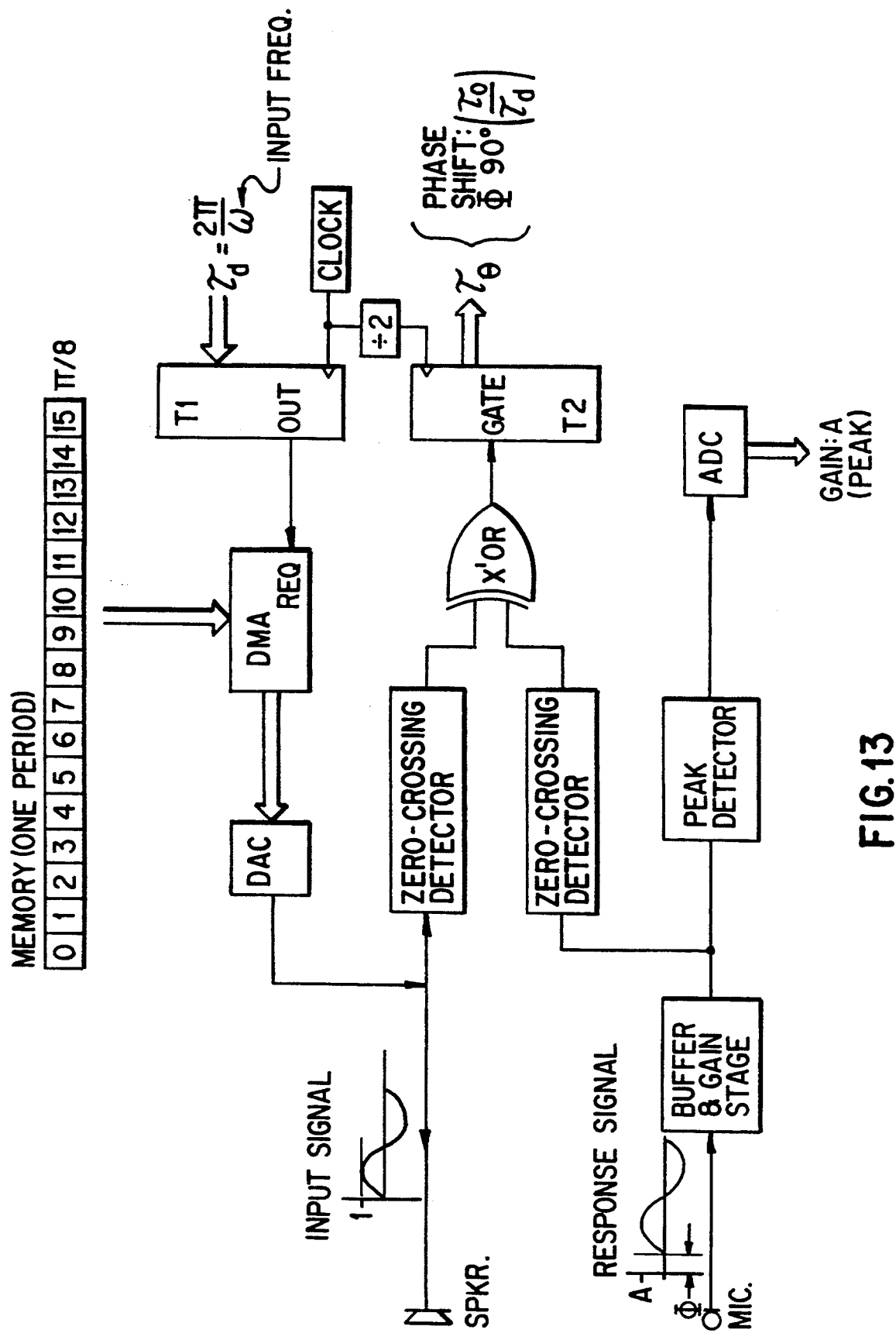
FIG. 13 is a more detailed block diagram of the signal processing circuitry.

FIG. 13 shows the signal processor (SP) of the resonance detection system in greater detail. The memory shown contains one sine-wave period, although as noted above in the preferred embodiment sixteen periods are stored. Timer T1 triggers the DMA, which in turn forwards a value from memory to the DAC. The output of the DAC is a sine wave that drives the speaker 22. The microphone 21 detects the response of the acoustic system, which is a sine wave that has a phase shift (Φ) and a gain (A) with respect to the signal driving the speaker 22. The response signal from the microphone 21 passes through a buffer and a gain stage, which removes any DC component from the microphone signal. This signal is then read by a zero-crossing detector (ZCD) and a peak detector (PD). Since the acoustic system being examined is an under-damped system, the first four periods of the sixteen period signal is ignored, so as to allow the acoustic system approach steady state. After the first four periods are ignored, the peak detector determines the greatest amplitude in the remaining twelve periods of the acoustic system's response.

Figure 14:
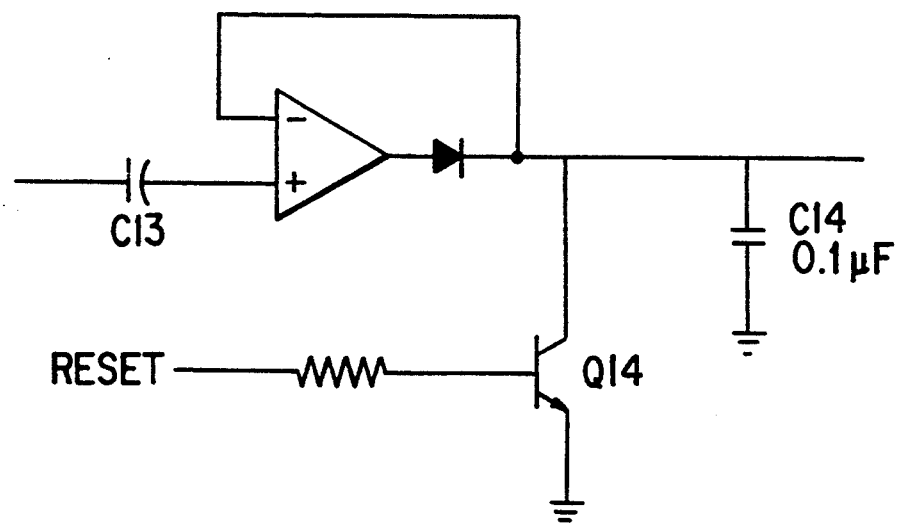
FIG. 14 shows a peak detector that may be used in the signal processor shown in FIG. 14.

FIG. 14 shows the peak-detector (PD), which measures the amplitude or gain at each frequency. The peak detector stores the magnitude in a capacitor C14, preferably a 0.1 μF polystyrene capacitor. A transistor switch Q14 allows the processor to ground the capacitor C14, thereby resetting the peak-detector after it has been read. The peak-detector is read by an 8-bit analog-to-digital converter (ADC).

The phase detector includes two zero-crossing detectors (ZCDs), which turn sinusoidal waves into square waves having the same frequency. (See P. Horowitz and W. Hill, *The Art of Electronics*, 2nd Ed., Cambridge University Press, 1989, p. 242, for an example of a zero-crossing detector.) One ZCD converts the input signal into a square wave, the other ZCD converts the response signal. The outputs of the ZCDs are provided to an exclusive-or gate. The output from the exclusive-or gate is a square wave, the width of which indicates the phase difference between the input signal and the response. If the two signals are completely in phase, the square wave pulse would have zero width. A 90° shift would cause a pulse width equal to one-half of the period of the driving frequency. The gate's output is used to gate a timer, T2. The counter counts when the signal is high, and does not when it is low. The counter is reset at the beginning of the sine-wave cycle, and read at the end of the cycle (EOC). The value read is the integrated phase angle. The buffer and gain stage elements in the signal processing circuit shown in FIG. 13 can vary the phase of the response signal by the time it reaches the ZCD and the X'OR gate. The microprocessor can take this additional phase shift into account in interpreting $\tau_\theta$.

FIG. 12 shows other components of the pump controller. The pump used may be the pump described in the Membrane-Based Rotary Peristaltic Pump Ser. No. 673,834, patent application, noted above, which may function as a control valve when turned off. The pump controller may receive error signals regarding signalling that the disposable cassette is mounted improperly (such as "door ajar" and "not vertical"). Also shown are communication lines leading to the user display and the power module. The power module includes an inductively coupled power supply, through which communications signals may be transmitted to other pump controllers being used for the same patient.

Figure 15:
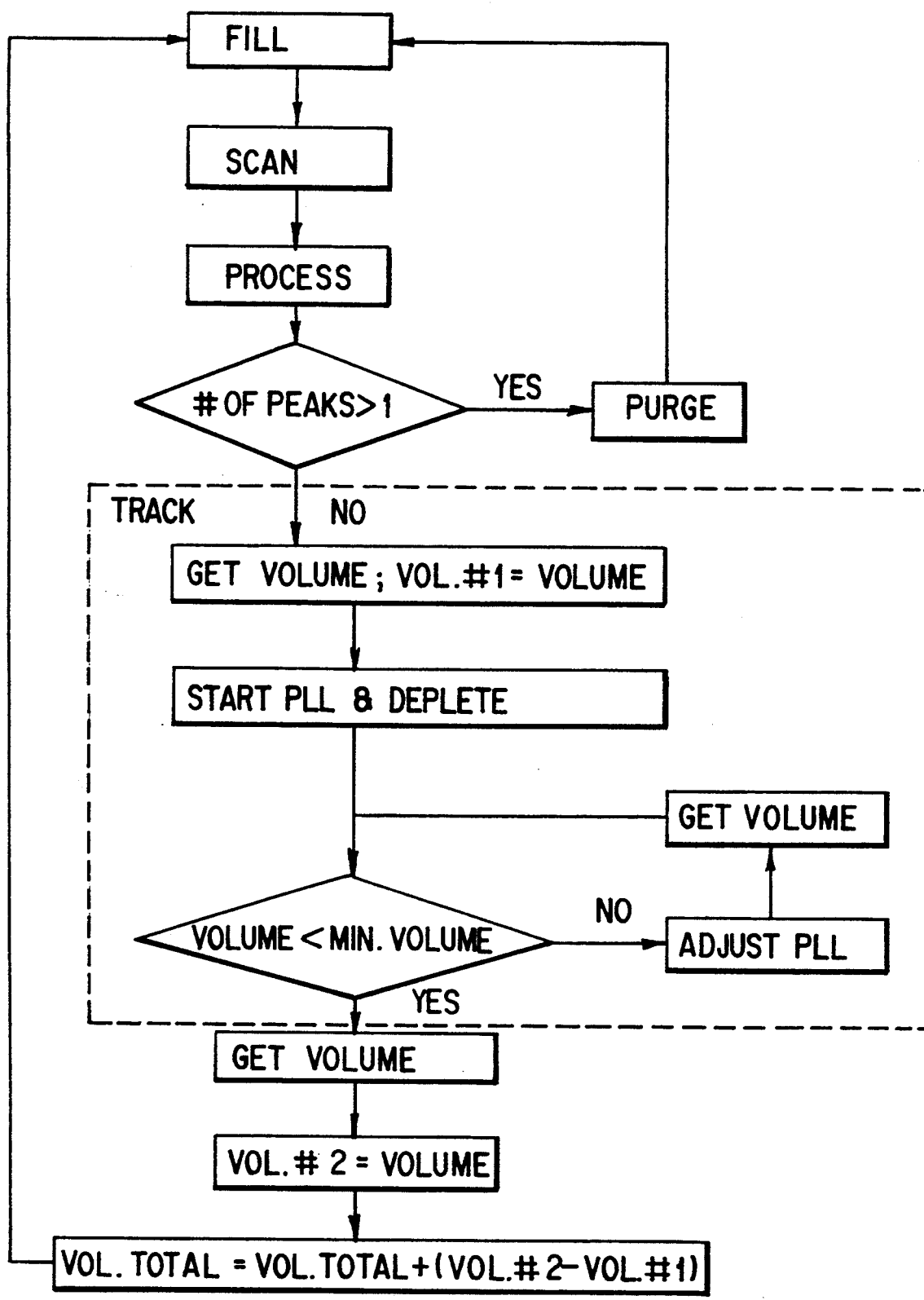
FIG. 15 is a flow chart showing the overall sequence of steps taken by the pump controller.

FIG. 15 is a flow chart showing a process for measuring the flow through the line 3 of the device shown in FIG. 8. In the FILL step valve 7 (valve B) is closed and valve 6 (valve A) is open. Fluid is allowed to flow into in the front chamber behind the membrane 85. The fluid may be pumped, or the head pressure may force it into the front chamber. Once the membrane is filled, valve 6 is closed. Then the SCAN mode is entered.

Figure 16:
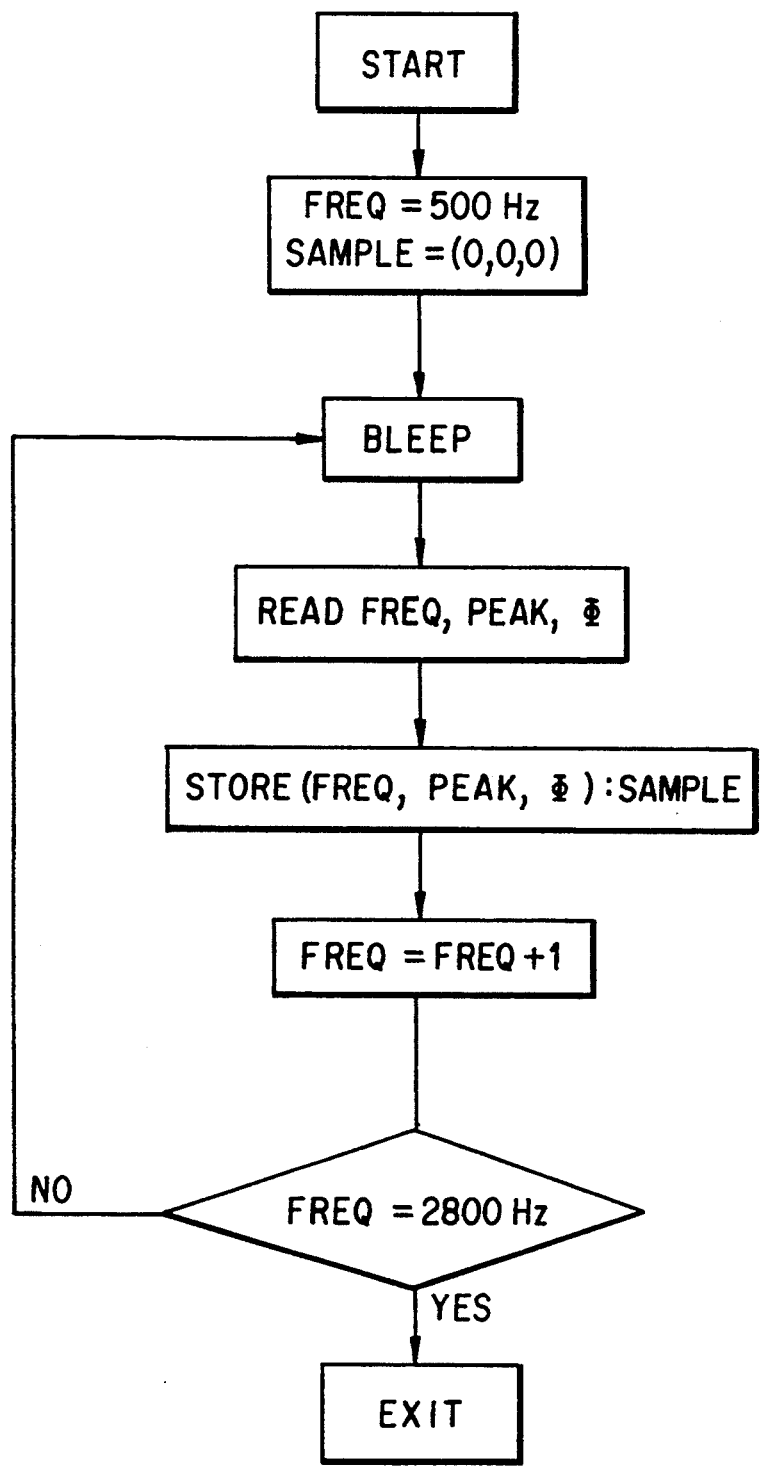
FIG. 16 is a flow chart showing the sequence of steps taken during the SCAN mode.

In the SCAN mode the gain and phase data for each frequency is stored in an array, as discussed above. FIG. 16 shows a flow chart for developing this array. Acoustic energy at a spectrum of frequencies between about 500 Hz and 2800 Hz is introduced into the back chamber, i.e. the acoustic system is "bleeped" at a numerous frequencies, one frequency at a time. The signal processing circuit shown in FIG. 13 is used to determine the phase shift and amplitude (peak) at each frequency. In the PROCESS step the microprocessor parses the array to find resonances, by locating rising edges, peaks and falling edges. The peaks are found by looking for high amplitudes surrounded by lower amplitudes. The symmetry, the Q-value and the band width of the peak are also examined by the microprocessor to ensure that the peak is created by a resonance and not noise. Between the rising and falling edges, the phase data is considered valid, and is used to finely resolve the center frequency.

The acoustic energy introduced into the back chamber, preferably does not have frequencies above 2800 Hz, and data above 2800 Hz is not collected. The speaker resonance is thereby avoided, and the detection of more than one resonance implies the existence of a bubble 81 in the liquid 52 in the front chamber 82. When a bubble is detected, it may be purged in the manner discussed above, and system returns to the FILL step of FIG. 15.

Once it is determined that the liquid 52 does not contain air bubbles, and assuming that there is a sufficient amount of liquid present in the chamber, the depletion cycle is begun, wherein volume $V_1$ is determined using a phase-locked-loop (PLL) in the TRACK mode, instead of the spectral analysis (SCAN and PROCESS) described above. Before valve 7 is opened, and the fluid 52 starts flowing out of the front chamber, the PLL is used to precisely determine $V_1$.

In the PLL mode a modified PLL is used to ascertain and track the volume, V1, of the gas-filled portion of the front chamber. PLLs typically consist of three basic elements: error detection, error integration (or low-pass filter) and feedback. Error detection is performed by the phase detector shown in FIG. 13. Integration is achieved by accumulating the phase error over twelve periods. (The integration functions as a low-pass filter, the time constant of which should preferably be a hundred times as large as that of the driving frequency for reasons of stability.)

Figure 17:
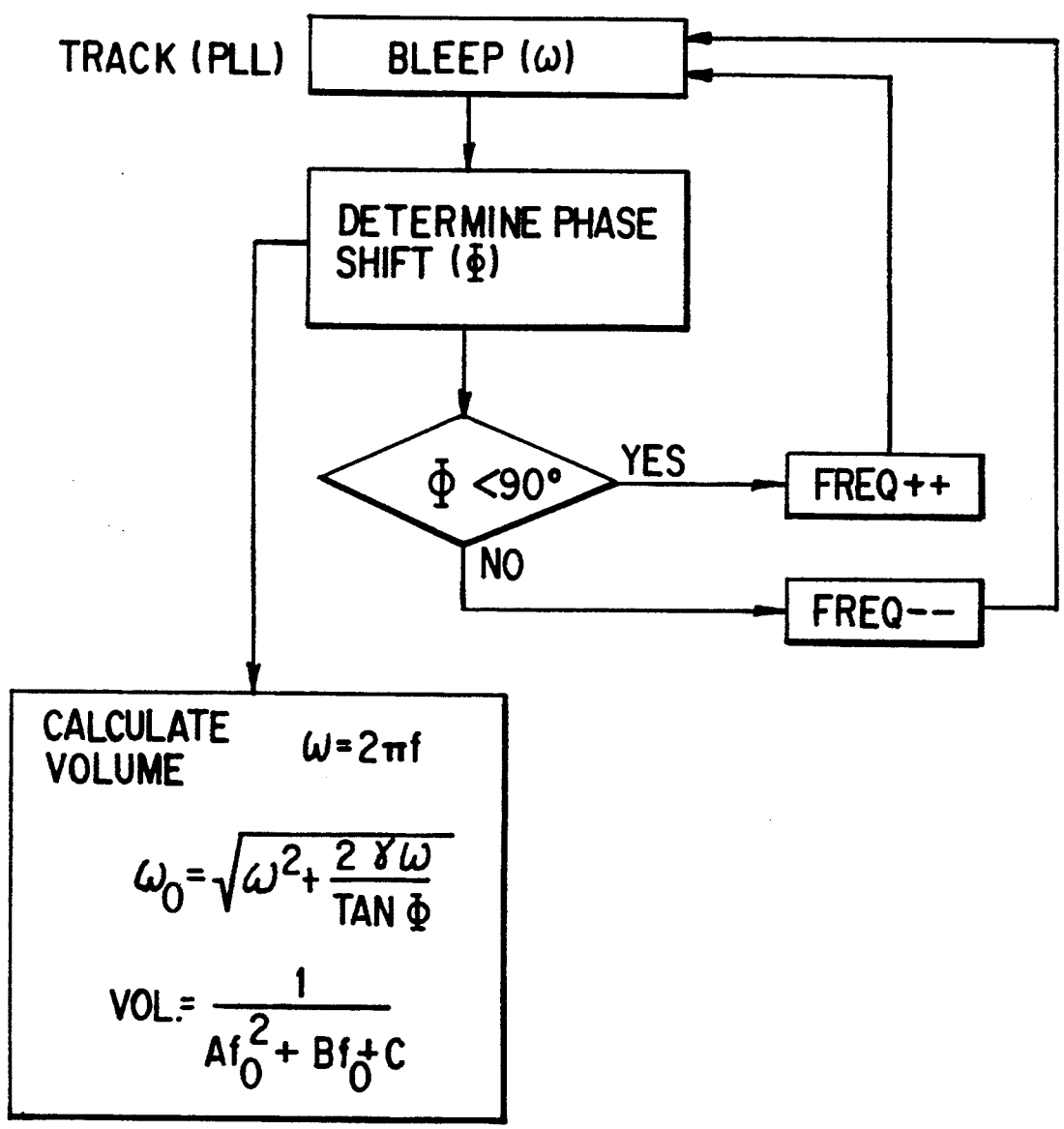
FIG. 17 is a flow chart showing the sequence of steps taken during the TRACK mode, which uses a modified phase-locked loop while the fluid in the chamber is being depleted.

The phase shift information is read by the microprocessor, which performs the feedback function in the PLL mode. The microprocessor uses the phase shift information to determine a new input frequency, and a corresponding $\tau_d$, which is fed to timer T1, which in turn triggers the DMA so as to create a sine wave of the desired frequency. FIG. 17 shows a flow chart of how the microprocessor closes the loop in the PLL mode. The acoustic system of FIG. 8 is bleeped at a frequency determined by the microprocessor. For the first iteration the resonant frequency determined in the PROCESS step of FIG. 15 is used. The signal processor shown in FIG. 13 is used to determine the phase shift ($\Phi$), and, based on this phase shift and the input frequency, the microprocessor calculates a more precise resonant frequency and from that the volume $V_1$, which is Vol #1 in FIG. 15.

Then valve 7 is opened, and the amount of fluid 52 in the front chamber depletes. The acoustic chamber is bleeped again at the more precise frequency just determined, or at a frequency that is very close. The signal processing circuit of FIG. 13 is used again to find the phase shift, and based on this phase shift the microprocessor determines whether to increase or decrease the input frequency. Another phase shift is determined for this new input frequency. This process continues, and the microprocessor tracks the resonant frequency, which is changing because volume $V_1$ is changing.

The microprocessor can from time to time use the phase shift information to update $V_1$. The microprocessor monitors the changing volume and phase shift. If the microprocessor determines that the membrane is depleting too quickly, it can partially close valve 7 so as to impede the flow. This is an important function, not only because one does not want to deliver medicine too quickly to the patient, but also because if the volume changes too quickly the microprocessor and the signal processing circuit of FIG. 13 may not be able to keep up. The amount of impedance valve 7 provides to the flow can be adjusted, so as to control the flow rate during depletion.

When $V_1$ reaches a certain size, valve 7 is closed, and the acoustic system is bleeped one more time at the frequency suggested by the last iteration of the PLL. The phase shift from this bleep and the frequency of the bleep is used to determine $V_1$, which is used as Vol. #2 in FIG. 15. Vol. #1 is subtracted from Vol. #2 to determine how the volume of fluid that flowed to the patient during the just-completed depletion cycle. This volume is added to the volume of fluid that has already been supplied to the patient. The fluid controller then returns to the FILL step, and the process is repeated.

In calculating the volume of the front chamber 82, corrections may be made for temperature and humidity, although such corrections are not thought to be necessary for most situations. Adapting equation (1) for the resonant angular frequency, $\Omega$, we derive:

$$4) \; \Omega^2 = S/\rho \; L \bullet \gamma/Vol = \gamma/\rho \bullet S/(L \bullet Vol)$$

Significantly, the square of speed of sound "c" is given by:

$$5) \; c^2 = \gamma/\rho$$

in units length$^2$/time$^2$. The units of the $S/(L \bullet Vol)$ are 1/length$^2$, yielding the product units of 1/time$^2$, which is frequency$^2$. Volume "Vol" is a function of the front and back chamber volumes, recalling eq. 4, which implies:

$$6) \; 1/Vol = 1/V_1 + 1/V_2$$

Hence, we see that frequency is determined by the speed of sound and an effective length, the reciprocal square root of the term "$A/(L \bullet Vol)$", a length determined by the overall geometry of the port and chambers. The sound-speed term comes entirely from the properties of air. Using an ideal gas approximation, which is quite accurate, the square of the speed of sound can be expressed as a function of air properties:

$$7) \; c^2 = \gamma RT/M \; \text{for}$$

$R$ = gas constant = $8.31437 \cdot 10^7$ erg °K.$^{-1}$ mol$^{-1}$ $T$ = absolute temperature in °K.

$M$ = average molecular weight of air + water vapor

= 28.966 gm mol$^{-1}$, dry air

= 18.015 gm mol$^{-1}$, water vapor

Hence, we may rewrite the result of eq. 10 as follows:

$$8) \; \Omega^2 = \gamma RT/M \bullet S/(L \bullet Vol)$$

The heat capacity ratio "$\gamma$" is dependent on water vapor content, like "M". To compute "$\gamma$", one must compute $C_v$, heat capacity at constant volume, as a weighted average of $C_v$ for air and $C_v$ for water vapor, proportioning the water vapor contribution to the saturation partial pressure of water vapor at temperature T, multiplied by the relative humidity fraction. With the weighted average $C_v$, one uses the relation that $$9) \; \gamma^2 = 1 + R/C_v \; \text{for}$$

$C_v = 20.6317 \cdot 10^7$ erg °K.$^{-1}$, dry air

= $25.4830 \cdot 10^7$ erg °K.$^{-1}$ mol$^{-1}$, water vapor

The effect of relative humidity rises steeply with temperature, since the absolute water content of air at a given relative humidity rises with temperature. Eq. 16 gives the partial pressure of water vapor, in atmospheres, at relative humidity=RH and at absolute temperature T in °K.:

$$10) \; ATM_{H20} = RH \cdot 10^{A/T+B)}$$

for $A = -2290.6$ $B = 6.17658$

The A and B coefficients are adjusted for an exact fit at 20° C. and 40° C., yielding a worst-case fractional error of −0.26% at 30° C. For computations at one atmosphere, weighted averages of air and water vapor properties are formed by weighting the air figure by (1-ATM$_{H20}$) and the water vapor figure by ATM$_{H20}$.

At 40° C.=104° F., the maximum perturbation on volume calibration attributable to humidity is at ±0.9% variation for relative humidities of 10% and 90% and calibration at 50%. Neglecting the effect of humidity, resonant frequency depends on the ratio "Vol/T", so calibration to absolute temperature is essential. Pressure does not enter into the calibration, so altitude and barometer can be ignored. Rapidly changing pressure, as might be used for pumping of the fluids being measured, cannot be entirely ignored. The critical factor with time-varying pressure is that the variation be slow enough to allow chamber air to equilibrate thermally with the chamber and orifice walls, which act as "infinite" heat sinks. The time constants involved will be quantified below.

The boundary layer is an acoustic orifice is driven by audio-frequency pressure variations. When the flow is being reversed rapidly, the maximum velocity achieved in a given direction is generally extremely small, which would imply a very low Reynolds number for pipe flow in a steady-flow analysis. This, in turn, would imply that orifice flow mechanics would be dominated by viscosity and the Q factor for the orifice would be much less than one. When the flow is being reversed rapidly, there are substantial pressure gradients in relation to the velocities achieved, and momentum effects tend to dominate over viscosity. It is as if high frequencies raise effective Reynolds numbers, emphasizing momentum forces over viscous forces. Fortunately, the equations for a one-dimensional boundary layer in oscillatory flow are relatively simple and yield a convenient algebraic solution, which will now be shown. To model the boundary layer near a static surface in a sinusoidally reversing flow, it is convenient to switch to a frame of reference in which the surface is oscillating tangentially and the fluid (e.g., air) at a distance from the surface is static. In this case, the sinusoidal tangential wall velocity "v" is described as a function of time "t" by a complex exponential times the amplitude A(0), the amplitude of height=0. In general, we have $A=A(Z)$, amplitude as a complex function of height Z above the oscillating surface, expressing both the amplitude and phase of the oscillating flow at Z:

11) $v(Z)=A(Z) \cdot EXP(j\omega t)$

The shear stress exerting a horizontal force across vertically adjacent layers of the oscillating fluid is proportional to the produce of the vertical gradient of horizontal velocity and the absolute viscosity, $\mu$, of the fluid:

12) $P=\mu \cdot \partial v/\partial Z$

Substituting the right side of eq. 11 and differentiating gives:

13) $P=\mu \cdot \partial A/\partial Z \cdot EXP(j\omega t)$

The net horizontal force per unit volume equals density "$\rho$" times acceleration, i.e. "$\rho$" times the derivative of velocity. This force/volume also equals the derivative of shear stress of P with respect to Z, i.e., the degree to which shear forces acting on the top and bottom surfaces of a layer of fluid are imbalanced:

14) $\rho \cdot \partial v/\partial t = \partial/\partial Z = \mu \cdot \partial^2 A/\partial Z^2 \cdot EXP(j\omega t)$ Substituting the right side of eq. 11 differentiated with respect to time, into the left side of eq. 14 yields:

15) $j\omega \rho \cdot A \cdot EXP(j\omega t) = \mu \cdot \partial^2 A/\partial Z^2 \cdot EXP(j\omega t)$ Dividing through the multipliers of $\partial^2 A/\partial Z^2$ and swapping sides yields:

16) $\partial^2 A/\partial Z^2 = (j\omega \rho/\mu) \cdot A$

The converging solution is readily seen to be the produce of wall velocity $A(O)$ times a decaying complex exponential:

17) $A(Z)=A(0) \cdot EXP(-Z/SQRT(\mu/j\omega\rho))$

The square root expression is divided into equal real and imaginary parts:

18) $SQRT(\mu/j\omega\rho)=SQRT(\mu/2\omega\rho)-j \cdot SQRT(\mu/2\omega\rho)$

A characteristic boundary layer depth can be defined as the real part of the square root expression in eq. 18:

19) $Z_0=SQRT(\mu/2\omega\rho)$

The flow field just described, decaying in amplitude and shifting in phase from a maximum velocity amplitude at a tangentially vibrating surface is toward zero amplitude at a large multiple of $Z_o$ above the surface, is now transformed into a uniformly vibrating flow field except in the vicinity of a surface, where the motion goes to zero. In this frame of reference, an oscillating horizontal pressure gradient must exist to maintain the flow oscillation, and this gradient is overcome progressively by a shear stress gradient on approach to the static surface. If the velocity field of the boundary layer is integrated from the surface upward to "infinity" or, in practice, a small multiple of $Z_o$, it can be shown that two perturbations affect the net flow. The "real" perturbation is that the net flow in phase with the prevailing flow outside the boundary layer is reduced as if he flow area had been reduced by the thickness $Z_o$. Hence, we may consider $Z_o$ to be a displacement thickness. The "imaginary" perturbation is a flow component 90° out of phase with the non-boundary flow field, moving in phase with the pressure gradient, as would occur if flow were limited by viscosity rather than inertia. For flow in a cylindrical orifice whose radius "R" is much greater than $Z_o$, the effective flow cross-section is reduced as if "R" were reduced by the amount $Z_o$. Simultaneously, a dissipative component of flow arises whose magnitude is the same as the "real" phase flow reduction magnitude. From these relationships, we obtain an expression for the orifice-Q, $Q_o$, in terms of radius R and thickness $Z_o$:

20) $Q_0=(R-Z_0)^2/(2 \cdot R \cdot Z_0)$

This description is, of course, valid only if $Z_o$ is a small fraction of R, i.e., for high $Q_o$. If $Z_o$ becomes too thick to satisfy this constraint, then one must solve the boundary layer equation in cylindrical coordinates. The solution for $Z_o >> R$ approaches the description of steady laminar flow in a short pipe, with a velocity distribution changing in phase with the driving pressure gradient and $Q_o$ approaching zero. The ratio of absolute viscosity, $\mu$, to density, $\rho$, designated $\rho v=\mu/\rho$, is given in the vicinity of room temperature by the expression:

21) $v=\mu/\rho=(0.1511$ $cm^2/sec)(T/293.16)^{1.863}/(P/1atm)$ for $T=°K.=°C.+273.16$, and P expressed in the same units as the value of 1 atmosphere in the denominator under P, e.g., $(P/1atm)=(mm.Hg/760)$.

Using this expression and eq. 19, we get $v=0.1511$ $cm^2/sec$ at 20° C. and $Z_o=0.00347$ cm. at 1 KHz and for orifice $R=0.15$ cm. This leads to $Q_o=20.6$.

In an acoustically vibrating cavity, the microfluctuations of acoustic pressure are accompanied by proportionate microfluctuations in temperature, due to the adiabatic nature of the compression and decompression. At the wall of the cavity, however, conditions are virtually isothermal, because solids have much greater thermal conductivity and thermal capacity than air. Very close to a wall, a thermal boundary layer occurs, representing a transition from adiabatic to isothermal compression and expansion. Significantly, the equations governing the thermal boundary layer have exactly the same form as the equations governing a vibrations flow boundary layer. The end equation of the analysis, analogous to flow eq. 16, for temperature variation $T_v$, is:

22) $\partial^2 T_v/\partial Z^2=(j\omega C/K) \cdot T_v$

Here C is heat capacity per unit volume and K is thermal conductivity. From this expression one obtains a characteristic thermal boundary layer thickness, $Z_t$, in an equation analogous to eq. 19:

23) $Z_t=SQRT(K/2\omega C\rho)$

The ration $K/C\rho$, called thermal diffusivity, bears a profound relationship to kinematic viscosity, $v=\mu/\rho$. The square root of either quantity, with units of length/$\sqrt{\text{time}}$ (e.g., cm/$\sqrt{\text{sec}}$) represents a diffusion distance that varies as the square root of time. Thermal diffusivity represents a diffusion of thermal energy, while kinematic viscosity represents a diffusion of kinetic energy, coupling adjacent layers of shearing air together. The ratio of the two quantities is not far from unity and changes little with temperature and negligibly with pressure:

24) $K/C_p = (1.3955 + 0.0005(T - 20° \text{ C.})) \cdot \mu/\rho$

The square root of this ratio relates thermal boundary layer thickness to flow boundary layer thickness, as expressed closely by a linear temperature fit:

25) $Z_t = (1.1813 + .0002(T - 20° \text{ C.})) \cdot Z_o$

The effect of the thermal boundary layer is to increases the compressibility of air over an effective thickness from $1/\gamma P$ to $1/P$. The fractional increment in compressibility is therefore $(1/P - 1/\gamma P)/(1/\gamma P) = \gamma - 1$. Hence, the volume displacement thickness of a thermal boundary layer is not $Z_o$ but $Z_t$ corrected for the fractional increase in volume. Designating this thermal displacement thickness as $Z_{td}$, we have:

26) $Z_{td} = (\gamma - 1) \cdot Z_t = (0.4758 + 0.00008(T - 20° \text{ C.})) \cdot Z_o$ The volume of a resonant cavity is effectively increased by the wall area multiplied by the displacement thickness $Z_{td}$. Accompanying this increase in acoustic compliance is an equal increment of compliance with a dissipative phase angle, representing the energy loss associated with heat flow across thermal resistance. Given these relationships, we can express an effective volume correction ratio and a chamber Q-factor, $Q_c$, in terms of Area/Vol and $Z_{td}$:

27) $\Delta Vol/Vol = Z_{td} \cdot Area/Vol$

28) $Q_c = (1 + \Delta Vol/Vol)/(\Delta Vol/Vol)$

For a cube, Area/Vol $= 6l^2/l^3$ for a side of length $l = Vol^{\frac{1}{3}}$. At a volume of 2 cm$^3$ and a frequency of 1 KHz, we obtain $Z_o = 0.00347$ cm (from above), $Z_{td} = 0.00165$ cm, $\Delta$ Vol/Vol $= .000786$, and $Q_c = 128$. For comparison, we recall an orifice $Q_o = 20.6$, giving $Q_c/Q_o = 6.2$. A practical front chamber is likely to have a higher surface/volume ratio than a cube, giving a smaller $Q_c$. Furthermore, the surface area is likely to change little when a fluid-backed diaphragm pushes into the chamber reducing volume, so that $Q_c$ will decrease with decreasing volume.

The Q of the larger back chamber will normally be higher than for the smaller front chamber. The overall chamber dissipation factor, $1/Q_c$, is a weighted average of the front and back chamber dissipation factors, $1/Q_{cf}$ and $1/Q_{cb}$, with the emphasis going to the smaller chamber, since energy of compression is higher there. The weighting should be:

29) $1/Q_c = ((1/Q_{cf})/Vol_f + (1/Q_{cb})/(Vol_b))/(1/Vol_f + 1/Vol_b)$

The dissipation factor for the entire resonant circuit is the sum of the dissipation factors of the inertia and spring components:

30) $1/Q = 1/Q_c + 1/Q_o$

The flow boundary layer reduces the effective orifice size, increasing the "inductive" or inertial impedance of the flow schematic, thus lowering resonant $\Omega$, while the thermal boundary layer increases the effective chamber volume, lowering the "capacitative" or spring impedance, again lowering $\Omega$. The fractional change in $\Omega^2$, which is used to determine Vol from eq. 8 is directly proportional to $1/Q$ at high Q, regardless of the relative chamber and orifice contributions to energy dissipation. This relationship might fail if Q is abnormally low due to a sharp flow obstruction or orifice edge, whose flow resistance might fail to obey the boundary layer equations described above. Similarly, dissipation in the speaker or microphone, or a leak from chamber to chamber to ambient, could lower the Q in a way that violates the stated relationship. For a clean leak-free acoustic resonator design with transducers that do not interfere significantly with resonant Q, however, the following resonant correction formula applies:

31) $\Omega^2_{ideal} = \Omega^2_{meas} \cdot (1 + 1/Q)$

In general, Q will be a relatively complicated function of frequency and the changing geometry of the front chamber. Eq. 31 implies a calibration correction function of frequency that can be based on the empirically measured Q of a resonant acoustic circuit. To determine the function $Q(\Omega)$ for computing front volumes, recall that the derivative of radian phase angle $\Phi$ with angular frequency $\omega$ in the vicinity of resonant frequency $\Omega$ is probably the best empirical measure of Q:

32) $Q(\Omega) = (\Omega/2) \cdot d\Phi/d\omega$ for $\omega$ varying near resonant $\Omega$.

This function can be calibrated for a typical volume measurement unit, or it can be determined directly for the system, during operation in the field, if provision is made electronically for causing a phase angle perturbation in the oscillator loop and observing the resulting frequency perturbation. An advantage to providing for actual Q determination during normal operation in the field is that any acoustic or electronic malfunction is likely to cause Q to depart from a normal range for the system. The orifice $Q_o$ needs to be known, separate from the overall Q of the acoustic circuit, in order to determine where the acoustic LC resonance lies in relation to the 90° phase resonance. Eqs. 19, 20, and 21 taken together give the orifice $Q_o$ as a function of geometry and frequency. The designer should reconcile the theory described above with actual circuit performance If the system is working properly, there should be a good correlation between theory and measurement, in which case an accurate calibration of front chamber volume from system frequency can be obtained using the equations described, plus a careful empirical calibration of the effective length for the given geometry.

The representation given above, with boundary layer equations to determine component values around a specified frequency, is fairly accurate from a few hundred hertz up to the vicinity of the piezo speaker resonance, around 3-4 KHz. At very low frequencies, where the computed Q factors for the circuit components fall below about 2, the boundary layer equations become invalid, being based on unlimited space above flat surfaces and not on confined space surrounded by enclosing surfaces. Going down in frequency, the orifice flow comes to resemble laminar flow in a short pipe, as mentioned above, with the impedance model coming to resemble a fixed resistance in series with a fixed inductance. At still lower frequencies, the thermal boundary layers reach to the centers of the chambers and compliance approaches a fixed isothermal compliance, or total capacitance of $C=Vol/P$, as opposed to the high-frequency adiabatic value of $C=Vol/\gamma P$. A good low-frequency limit circuit representation of a chamber would be obtained by adding, in parallel with the capacitor at $C=Vol/\gamma P$, a parallel R-series-C with the $C=(Vol/P)\cdot(1-1/\gamma)$. The R of this R-series-C should be chosen so that the 3 db frequency $1/RC$ equals the frequency $\omega$ at which the thermal boundary layer thickness $Z_t=Vol/Area$ of the chamber, using eqs. 25, 21, and 19. In the geometry being discussed by example, the thermal time constant RC is about 0.6 seconds for the front chamber, about 1.6 seconds for the back chamber, and about 0.025 seconds across the orifice radius, setting $Z_t=radius/2$, which equals Vol/area for a long cylinder. Thermal equilibration in the orifice is critical for accurate volume measurement. If a transient change in pumping pressure is a significant fraction of an atmosphere, the accompanying fractional change in absolute temperature will be of the same order of magnitude. Specifically, 33) $T/T_o=(P/P_o)^{(\gamma-1)/\gamma}$ for absolute temperature T relative to initial $T_o$ and total pressure P relative to initial $P_o$. As mentioned above, it is the ratio Vol/T that determines resonant frequency, but the temperature T that counts is T in the orifice, which determines the air density in the orifice and therefore the effective moving mass. Although the 0.025 second equilibrium time constant for air in the orifice is fairly fast, the situation is changed if a chamber is not at thermal equilibrium and air is flowing from that chamber into the orifice, dynamically keeping the average air temperature in the orifice away from equilibrium. Air will flow as the front chamber moves toward thermal equilibrium and changes volume, and air will flow as a result of fluid flowing into or out of the front chamber. Where pumping is taking place faster than one stroke every three or four seconds, there will be a systematic tendency to overestimate net pumped volume. At slightly lower pumping rates, volume estimates might be off when volume is dynamically changing, but readings should settle rapidly to true values when fluid flow stops and the standing air in the orifice equilibrates with the orifice walls.

By way of example, one can use measured frequency and temperature to compute volume.

First, for thermodynamic properties of air. Assume that regardless of operating temperature in the chambers the moisture content of the air in the orifice is the same as room-temperature air, 72° F., at 70% relative humidity. Then $T_c=(72-32)/1.8=22.22°$ C., which, adding 273.16° K. at 0° C. yields T=295.38° K. 70% relative humidity as a fraction is 0.7, so setting RH=0.7 and plugging into eq. 10 yields $ATM_{H20}=0.0185$, rounding to three figures. This figure is a reasonable estimate wherever air in the apparatus originates from a climate-controlled indoor environment. Even if the temperature chambers is significantly different due to local sources of heat or cold, the fraction 0.0185 is likely to be a good estimate of fractional water content of air. With this figure and the figures given following Eq. 7 for molecular weight, a weighted-average molecular weight of dry air and water vapor is obtained.

$M=(28.966)(1-0.0185)+(18.015)(0.0185)=28.763$

This figure differs from dry air by only 0.7%. Similarly computing heat capacity at constant volume, $C_v$, as a weighted average of the dry air and water figures following Eq. 9, we obtain:

$C_v=(20.6317\cdot10^7)(1-0.0185)+(25.48-30\cdot10^7)(0.0185)=20.7214\cdot10^7$

This figure differs from dry air by only 0.4%. Using the figure for the gas constant R given following Eq. 7, we use Eq. 9 to solve for the ratio $\gamma$:

$\gamma=1+8.31437\cdot10^7/20.7214\cdot10^7=1.40125$

All these figures can be taken as fixed constants for volume calculations based on a climate-controlled room temperature air.

Now temperature and frequency are used to determine front-chamber volume. For calibration we shall use the figures:

$Vol_{front}=2.00$ cm$^3$=front chamber volume
$Vol_{back}=12.00$ cm$^3$=back chamber volume
$R_{orifice}=0.15$ cm=orifice radius
$l_{orifice}=0.6$ cm=orifice length
T=298.16° K.=assumed chamber temperature of 25° C.=77° F.

The chamber temperature is not the same figure as was used to compute moisture content or air, but is a local, measured chamber temperature. From these orifice area may be computed:

$A=\pi R^2=0.070686$ cm$^2$ and an effective length of actual length+diameter is used:

$l_{eff}=l+2R=0.6+2(0.15)=0.9$ cm

Combining A and l gives an orifice dimension:

$A/l_{eff}=0.070686/0.9=0.0784540$ cm

Reduced volume Vol is given by Eq. 6, which for the nominal figures given works out to:

$1/Vol=\frac{1}{2}+1/12=0.58333$ cm$^{-3}$

Computing theoretical resonant frequency for an infinite-Q system at 25° C.=298.16° K. (=77° F.), Eq. 8:

$\Omega^2 = \gamma RT/M \cdot A/l_{eff} \cdot 1/Vol$ $= 1.40125 \cdot 8.31437 \cdot 10^7 \cdot 298.16 \cdot (1/28.763) \cdot$ $.078540 \cdot .58333$ $= 55,3331,000$ $f = 1183.9$ Hz In a calibration measurement, resonance was:

f=948 Hz@maximum volume=2 cm$^3$ $\Omega=2\pi f=5956.46$ s$^{-1}$

The computed frequency is high by 25%. Calibrating to actual measured frequency response at maximum volume, ignore the geometric computation of $A/l_{eff}$ and use, instead, a value for $A/l$ from Eq. 8:

$$A/l = \Omega^2/(\gamma RT/M \bullet 1/Vol) = 005036 \text{ cm}$$

Given a measured frequency and temperature for an unknown volume, solve Eq. 8 for $1/Vol$:

$$1/Vol = \Omega^2/(\gamma RT/M \bullet A/l)$$

Then, applying Eq. 6, solve for $Vol_{front}$:

$$Vol_{front} = 1/(1/Vol - 1/Vol_{back})$$

To obtain a more exact solution, compute a theoretical value for the orifice quality factor, $Q_o$, using Eqs. 19, 20, and 21. First, from Eq. 21, at $T=298.16$, kinematic viscosity may be determined:

$$\nu = \mu/\rho = (0.1511)(298.16/293.16)^{1.863}/((latm/latm) = 0.1537 \text{ cm}^2/\text{sec}$$

Substituting into Eq. 19, boundary layer thickness is determined:

$$Z_o = SQRT(0.1537/2\omega) = 0.003592 \text{ cm}$$

From Eq. 20 we obtain orifice Q:

$$Q_o = (0.15 - 0.003592)^2/(2 \bullet 0.15 \bullet 0.003592 = 19.89$$

At the true "LC" resonance, the phase measured in the acoustic circuit should be:
ANGLE(H($\Omega$)) = ATAN(19.89) = 87.122°, or 2.878° off 90°.
The phase-lock loop circuit tracks a circuit phase angle of 90°, which gives a frequency slight above resonance. The phase-dither adds a capacitance of 680 $pf$ in parallel with a resistor of 100 K$\Omega$, giving a $-3$ db frequency of 2340 Hz. The frequency of the circuit is observed to drop by 10 Hz to 938 Hz. At this frequency, the phase angle across the RC is:
DITHER = ATAN(938/2340) = 21.84° phase shift = 0.3812 radians phase shift
Eq. 32 gives overall circuit Q as a function of radian phase shift $d\Phi$ per fractional change in frequency, $d\omega/\Omega$, with a factor of $\frac{1}{2}$. The frequency in Hz can be used instead of radian frequency, since the $2\pi$ factor divides out:

$$Q = (948/2) \bullet 0.3812/10 = 18.07$$

This measured value correlates well with theory. The theoretical front chamber Q from above was 128, which dominates the overall chamber Q by 5 parts out of 6. The back chamber has a larger volume but a more irregular shape, so its surface/volume ratio is probably comparable, implying about the same Q. Adding $1/Q$ dissipation factors, one obtains Theoretical $Q = 1/(1/19.89 + 1/128) = 17.215$ This is low by 4.7% compared to the dither value.

Using $Q_o = 19.89$ and $Q = 18.07$ for orifice and overall Q-factors, we determine first the frequency at 90° phase, and then the corrected resonance frequency, taking boundary layer effects into account. We can substitute frequency "f" in Hz for frequency "$\omega$" in radians/second into Eq. 32, since the ratio cancels the factor of $2\pi$. Hence, an expression for $d\Phi/d\theta$ is written and solved:

$$d\Phi/df = 2Q/f = 2(18.07)/948 = 0.03812 \text{ radians/Hz}$$

Recalling from above:
ANGLE(H($\Omega$)) = ATAN(19.89) = 87.122°, or 2.878° = 0.05023 radians off quadrature
The deficit angle from quadrature of 0.05023 radians implies a frequency correction from observed phase-look frequency to true resonance:

$$f_{resonant} = f_p + (\pi/2 - ATAN(-Q_o))/d\Phi/df = 948 + (0.05023/0.03812) = 949.32$$

The phase error between tracked quadrature phase and the resonance LC phase goes as $1/Q_c$, and the frequency correction per unit of phase error goes as $f/(2 \bullet Q)$, so that an asymptotic expression for the resonance correction at high Q is expressed simply:

$$f_{resonant} = f_{pH} \times (1 + 1/(2 \bullet Q_o \bullet Q)) = 948(1 + 1/(2 \bullet 18.07 \bullet 19.89)) = 949.32$$

This approximation matches the more exact solution to 5 place accuracy. Now compute

| | | | |
|---|---|---|---|
| $\Omega$ | $= 2\pi \cdot 949.32 =$ | 5964.75 | partially corrected |
| $\Omega^2$ | $=$ | 35,578,000 | partially corrected | and from Eq. 31, using the overall Q determined by phase dither to correct to an ideal frequency for volume computation, one obtains:
$\Omega^2 = 35,578,000 \bullet (1 + 1/18.07) = 37,547,000$ fully corrected From this point, the computation proceeds exactly as in the no-boundary-layer case,, but using the corrected radian-frequency-squared rather than the electronically measured radian-frequency-squared to compute $Vol_{front}$.

In the boundary layer corrected context, the effective orifice dimension $A/l$ can be computed from the corrected value of $\Omega^2$, and the frequency measured at unknown volume can be corrected in like manner.

This result is based on the temperature T measured at the time the frequency was sampled, and it is based on a measurement of frequency dither from a frequency close to the current frequency. It is not necessary to perform the dither measurement every time that volume is computed. The overall Q of the system is likely to be a fairly consistent function of frequency, so that the dither Q can be expressed in a table, applicable to all units sharing the software, with actual dither Q only checked occasionally, as assurance of system integrity.

What is claimed is:

1. A system for controlling the flow of liquid through a line, the system comprising:
a chamber disposed in the line, wherein the chamber has an inlet from the line and an outlet to the line, wherein the chamber houses a volume of gas in communication with liquid in the chamber;
isolation means for isolating in the chamber a volume of liquid from pressure effects of liquid in the rest of the line and for dispensing liquid from the chamber, wherein the isolation means includes a first valve means, located at the inlet, for selectively permitting and preventing flow into the chamber, and a second valve means, located at the outlet, for selectively permitting and preventing flow out of the chamber;

resonance means for associating with the chamber a resonatable mass of known acoustic characteristics, associated with the chamber, so as to form an acoustic resonant system;

detection means for determining a frequency of self-resonance of the system, and, based on the frequency of self-resonance, the volume of gas in the chamber; and control means, in communication with the first and second valve means and the detection means, for receiving information regarding the volume of gas in the chamber and directing the operation of the first and second valve means in order to measure and control flow of liquid through the line.

2. A system according to claim 1, wherein the control means causes
   (i) the second valve means to prevent flow out of the chamber,
   (ii) the first valve means to permit flow into the chamber, while the second valve means prevents flow,
   (iii) the first valve means to prevent flow, after liquid has flowed into the chamber,
   (iv) the detection means to determine the volume of gas in the chamber, while both the first and second valve means are closed,
   (v) the second valve means to permit flow from the chamber after the volume has been determined, and
   (vi) the detection means to determine the volume of gas in the chamber after the second valve means has permitted liquid to flow from the chamber.

3. A system according to claim 1, wherein the detection means includes:
   means for generating electrical signals, each having one of a variety of frequencies;
   means for converting each of the electrical signals into an acoustic response in the chamber;
   means for determining a phase change of an acoustic response with respect to its corresponding electrical signal;
   means for determining an amplitude of the acoustic response with respect to its corresponding electrical signal;
   means for storing in an array the phase change and amplitude for each frequency;
   means for determining, based on the array, whether a frequency is a resonant frequency of the acoustic resonant system; and
   means for determining, based on a resonant frequency, the volume of gas in the chamber.

4. A system according to claim 1, wherein the detection means includes:
   means for generating an electrical signal having a frequency;
   means for converting the electrical signal into an acoustic response in the chamber;
   means for determining a phase change of the acoustic response with respect to the electrical signal; and
   means for determining, based on the frequency and the phase change, the volume of gas in the chamber.

5. A system according to claim 1, wherein the detection means includes:
   means for generating electrical signals having a variety of frequencies;
   means for converting electrical signals into an acoustic response in the chamber;
   means for determining a phase change of an acoustic response with respect to the electrical signal causing the acoustic response;
   means for determining an amplitude of an acoustic response with respect to the electrical signal causing the acoustic response;
   means for storing in an array phase changes and amplitudes for a spectrum of frequencies;
   means for determining, based on the array, a preliminary resonant frequency of the acoustic resonant system;
   means for determining, based on the frequency and the phase change of the acoustic response caused by an electrical signal having as a frequency the preliminary resonant frequency, the volume of gas in the chamber.

6. A system according to claim 1, further including pressure means for varying the pressure of the gas in the chamber in order to pull liquid into or force liquid out of the region, and wherein the control means also directs the operation of the pressure means to produce the desired flow through the line.

7. A system for controlling the flow of liquid through a line, the system comprising:
   a chamber disposed in the line, wherein the chamber has an inlet from the line and an outlet to the line, wherein the chamber houses a volume of gas in communication with liquid in the chamber;
   isolation means for isolating in the chamber a volume of liquid from pressure effects of liquid in the rest of the line and for dispensing liquid from the chamber, wherein the isolation means includes a first valve means, located at the inlet, for selectively permitting and preventing flow into the chamber, and a second valve means, located at the outlet, for selectively permitting and preventing flow out of the chamber;
   a resonatable mass of known acoustic characteristics, associated with the chamber, so as to form an acoustic resonant system;
   signal means for generating an electrical signal having a spectrum of frequencies;
   acoustic means for converting the electrical signal into an acoustic response in the chamber;
   detection means for determining whether a frequency in the spectrum causes the resonatable mass to resonate, and calculating, based on a determined resonant frequency, the volume of gas in the chamber; and
   control means, in communication with the first and second valve means and the detection means, for receiving information regarding the volume of gas in the chamber and directing the operation of the first and second valve means in order to measure and control flow of liquid through the line.

8. A system according to claim 7, further including measurement means for measuring, at a frequency in the spectrum, gain of the acoustic response relative to the electrical signal; and wherein the detection means determines whether a frequency is resonant, based on the gain of the acoustic response at the frequency.

9. A system according to claim 8, wherein the measurement means further includes means for measuring a phase angle of the acoustic response relative to the electrical signal, and wherein the detection means determines whether a frequency causes the resonatable mass to resonate, based on the phase angle and the gain of the acoustic response at that frequency.

10. A system according to claim 7, wherein the detection means includes:
means for determining a phase change of an acoustic response with respect to its corresponding electrical signal;
means for determining an amplitude of the acoustic response with respect to its corresponding electrical signal;
means for storing in an array the phase change and amplitude for each frequency;
means for determining, based on the array, whether a frequency is a resonant frequency of the acoustic resonant system; and
means for determining, based on a resonant frequency, the volume of gas in the chamber.

11. A system according to claim 7, further including pressure means for varying the pressure of the gas in the chamber in order to pull liquid into or force liquid out of the region, and wherein the control means also directs the operation of the pressure means to produce the desired flow through the line.

12. A system for controlling the flow of liquid through a line, the system comprising:
a chamber disposed in the line, wherein the chamber houses a volume of gas in communication with liquid in the chamber;
isolation means for isolating in the chamber a volume of liquid from pressure effects of liquid in the rest of the line and for dispensing liquid from the chamber;
a resonatable mass of known acoustic characteristics, associated with the chamber, so as to form an acoustic resonant system;
signal means for generating an electrical signal having a spectrum of frequencies;
acoustic means for converting the electrical signal into an acoustic response in the chamber; and
detection means for determining whether a frequency in the spectrum causes the resonatable mass to resonate, and calculating, based on a determined resonant frequency, the volume of gas in the chamber;
wherein the detection means further includes means for determining, based on a determined resonant frequency, the presence of a gas-bubble in the liquid.

13. A system according to claim 12, wherein the detection means includes:
means for determining a phase change of an acoustic response with respect to its corresponding electrical signal;
means for determining an amplitude of the acoustic response with respect to its corresponding electrical signal;
means for storing in an array the phase change and amplitude for each frequency;
means for determining, based on the array, whether a frequency is a resonant frequency of the acoustic resonant system;
means for determining, based on a resonant frequency, the presence of a gas-bubble in the liquid; and means for determining, based on the resonant frequency, the volume of gas in the chamber.

14. A system for controlling the flow of liquid through a line, the system comprising:
a chamber disposed in the line, wherein the chamber houses a volume of gas in communication with liquid in the chamber;
isolation means for isolating in the chamber a volume of liquid from pressure effects of liquid in the rest of the line and for dispensing liquid from the chamber;
a resonatable mass of known acoustic characteristics, associated with the chamber, so as to form an acoustic resonant system;
signal means for generating an electrical signal having a spectrum of frequencies;
acoustic means for converting the electrical signal into an acoustic response in the chamber;
detection means for determining whether a frequency in the spectrum causes the resonatable mass to resonate, and calculating, based on a determined resonant frequency, the volume of gas in the chamber; and
measurement means for measuring, at a frequency in the spectrum, gain of the acoustic response relative to the electrical signal;
wherein the detection means determines whether a frequency is resonant, based on the gain of the acoustic response at the frequency; and
wherein the detection means further includes means for determining, based on a determined resonant frequency, the presence of a gas-bubble in the liquid.

15. A system for controlling the flow of liquid through a line, the system comprising:
a chamber disposed in the line, wherein the chamber houses a volume of gas in communication with liquid in the chamber;
isolation means for isolating in the chamber a volume of liquid from pressure effects of liquid in the rest of the line and for dispensing liquid from the chamber;
a resonatable mass of known acoustic characteristics, associated with the chamber, so as to form an acoustic resonant system;
signal means for generating an electrical signal having a spectrum of frequencies;
acoustic means for converting the electrical signal into an acoustic response in the chamber;
detection means for determining whether a frequency in the spectrum causes the resonatable mass to resonate, and calculating, based on a determined resonant frequency, the volume of gas in the chamber; and
measurement means for measuring, at a frequency in the spectrum, gain of the acoustic response relative to the electrical signal, wherein the measurement means further includes means for measuring a phase angle of the acoustic response relative to the electrical signal;
wherein the detection means determines whether a frequency causes the resonatable mass to resonate, based on the phase angle and the gain of the acoustic response at that frequency; and
wherein the detection means further includes means for determining, based on a determined resonant frequency, the presence of a gas-bubble in the liquid.

* * * * *